US010736560B2

(12) United States Patent
Haugland et al.

(10) Patent No.: US 10,736,560 B2
(45) Date of Patent: Aug. 11, 2020

(54) AUTOMATIC DETECTION OF TEETH CLENCHING AND/OR TEETH GRINDING

(71) Applicant: Sunstar Suisse SA, Etoy (CH)

(72) Inventors: Morten Haugland, Svenstrup J (DK); Christian Christiansen, Birkerod (DK); Nao Takano, Lausanne (CH)

(73) Assignee: Sunstar Suisse SA, Etoy (CH)

(*) Notice: Subject to any disclaimer, the term of this patent is extended or adjusted under 35 U.S.C. 154(b) by 396 days.

(21) Appl. No.: 15/309,301

(22) PCT Filed: May 7, 2015

(86) PCT No.: PCT/EP2015/060091
§ 371 (c)(1),
(2) Date: Nov. 7, 2016

(87) PCT Pub. No.: WO2015/169914
PCT Pub. Date: Nov. 12, 2015

(65) Prior Publication Data
US 2017/0071529 A1 Mar. 16, 2017

(30) Foreign Application Priority Data
May 7, 2014 (EP) .................................. 14167357

(51) Int. Cl.
A61B 5/00 (2006.01)
A61B 5/0488 (2006.01)
(Continued)

(52) U.S. Cl.
CPC .......... A61B 5/4557 (2013.01); A61B 5/0476 (2013.01); A61B 5/0488 (2013.01);
(Continued)

(58) Field of Classification Search
CPC ... A61B 5/0488; A61B 5/6814; A61B 5/7257; A61B 5/04015
(Continued)

(56) References Cited

U.S. PATENT DOCUMENTS 4,669,477 A * 6/1987 Ober .................. A61N 1/36017
600/590
4,715,367 A * 12/1987 Crossley ................ A61B 5/113
600/27
(Continued)

FOREIGN PATENT DOCUMENTS

JP 2006521844 A 9/2006
WO WO-1998/031277 A1 7/1998
(Continued)

Primary Examiner — May A Abouelela
(74) Attorney, Agent, or Firm — Dinsmore & Shohl LLP

(57) ABSTRACT

The present disclosure provides a computer implemented method for automatic detection of teeth clenching and/or teeth grinding in a dataset representing the level of biting force vs. time of a subject, the method comprising the steps of a) calculating a threshold level of biting force assigned to time $t=t_1$ based on a background level determined from the dataset at a prior time $t=t_1-T_{back}$, where $T_{track}$ is a first predefined period of time, b) checking the level of biting, and if the level of biting force at time, t, exceeds the threshold level assigned to time t for a second predefined period of time, $T_{clench/grind}$, then assigning an event of teeth clenching to time t, c) if an event of teeth clenching has been assigned to time t, then either waiting a predefined period of time 10 $T_{wait}$, or waiting until the level of biting is below the threshold for another predefined period of time $T_{end}$, d) if no events of teeth clenching and/or teeth grinding have been assigned for a third predefined period of time $T_{silence}$, then repeating steps a)-c), e) if events of teeth clenching and/or teeth grinding have been assigned for a third predefined period of time $T_{silence}$, then repeating only steps b)-c).

21 Claims, 15 Drawing Sheets

(51) Int. Cl.
*A61B 5/22* (2006.01)
*A61B 5/1495* (2006.01)
*A61B 5/0476* (2006.01)
*A61B 5/11* (2006.01)
*A61B 7/00* (2006.01)
*A61F 5/56* (2006.01)

(52) U.S. Cl.
CPC .............. *A61B 5/11* (2013.01); *A61B 5/1495* (2013.01); *A61B 5/228* (2013.01); *A61B 5/4519* (2013.01); *A61B 5/486* (2013.01); *A61B 5/726* (2013.01); *A61B 5/7235* (2013.01); *A61B 5/7257* (2013.01); *A61B 5/7264* (2013.01); *A61B 7/006* (2013.01); A61B 2560/0223 (2013.01); A61B 2562/0219 (2013.01); A61B 2562/0261 (2013.01); A61F 2005/563 (2013.01)

(58) Field of Classification Search
USPC ............... 600/300, 310, 587, 590, 544–546; 607/48
See application file for complete search history.

(56) References Cited

U.S. PATENT DOCUMENTS

| | | | | |
|---|---|---|---|---|
| 4,838,283 A * | 6/1989 | Lee, Jr. | ................... | A61F 5/566 128/859 |
| 4,989,616 A * | 2/1991 | Lee, Jr. | ................... | A61B 7/001 128/859 |
| 4,995,404 A * | 2/1991 | Nemir | .................... | A61B 5/224 600/590 |
| 5,078,153 A * | 1/1992 | Nordlander | .......... | A61B 5/0002 128/905 |
| 5,265,624 A * | 11/1993 | Bowman | ................ | A61B 5/113 128/848 |
| 5,540,733 A * | 7/1996 | Testerman | ........... | A61B 5/1135 600/529 |
| 5,553,626 A * | 9/1996 | Burger | .................... | A61F 5/566 600/587 |
| 5,766,124 A * | 6/1998 | Polson | ................... | A61N 2/006 600/13 |
| 6,076,011 A * | 6/2000 | Hoover | ................ | A61B 5/0488 600/546 |
| 6,093,158 A * | 7/2000 | Morris | ..................... | A61B 5/11 600/590 |
| 6,270,466 B1 * | 8/2001 | Weinstein | ........... | A61B 5/0488 600/590 |
| 6,597,944 B1 * | 7/2003 | Hadas | .................. | A61B 5/0488 60/587 |
| 6,638,241 B2 * | 10/2003 | Yerushalmy | ....... | A61N 1/36014 600/590 |
| 8,016,776 B2 * | 9/2011 | Bourget | ............... | A61B 5/0002 600/587 |
| 8,308,661 B2 * | 11/2012 | Miesel | .................. | A61B 5/1116 600/587 |
| 8,579,794 B2 * | 11/2013 | Henke | ...................... | A61F 5/56 600/27 |
| 2004/0193068 A1* | 9/2004 | Burton | ................. | A61B 5/0476 600/544 |
| 2005/0076908 A1* | 4/2005 | Lee | ...................... | A61B 5/0809 128/204.23 |
| 2005/0080463 A1* | 4/2005 | Stahmann | ........... | A61B 5/0488 607/62 |
| 2006/0184059 A1* | 8/2006 | Jadidi | ................ | A61B 5/04015 600/546 |
| 2008/0243023 A1* | 10/2008 | Valkhof | .................. | A61F 5/566 600/546 |
| 2010/0063350 A1* | 3/2010 | Henke | ................ | A61B 5/02055 600/28 |
| 2011/0105941 A1* | 5/2011 | Jadidi | .................. | A61B 5/0488 600/546 |
| 2011/0118581 A1* | 5/2011 | Jadidi | .................. | A61B 5/0492 600/372 |
| 2011/0288445 A1* | 11/2011 | Lillydahl | ............ | A61B 5/0488 600/590 |
| 2012/0271190 A1* | 10/2012 | Mortensen | ........... | A61B 5/0488 600/546 |

FOREIGN PATENT DOCUMENTS

| | | |
|---|---|---|
| WO | WO-2002/049534 | 6/2002 |
| WO | WO-2004/087258 A1 | 10/2004 |
| WO | 2011114526 A1 | 9/2011 |
| WO | WO-2013/006728 A2 | 1/2013 |
| WO | WO-2013/017985 A1 | 2/2013 |

* cited by examiner

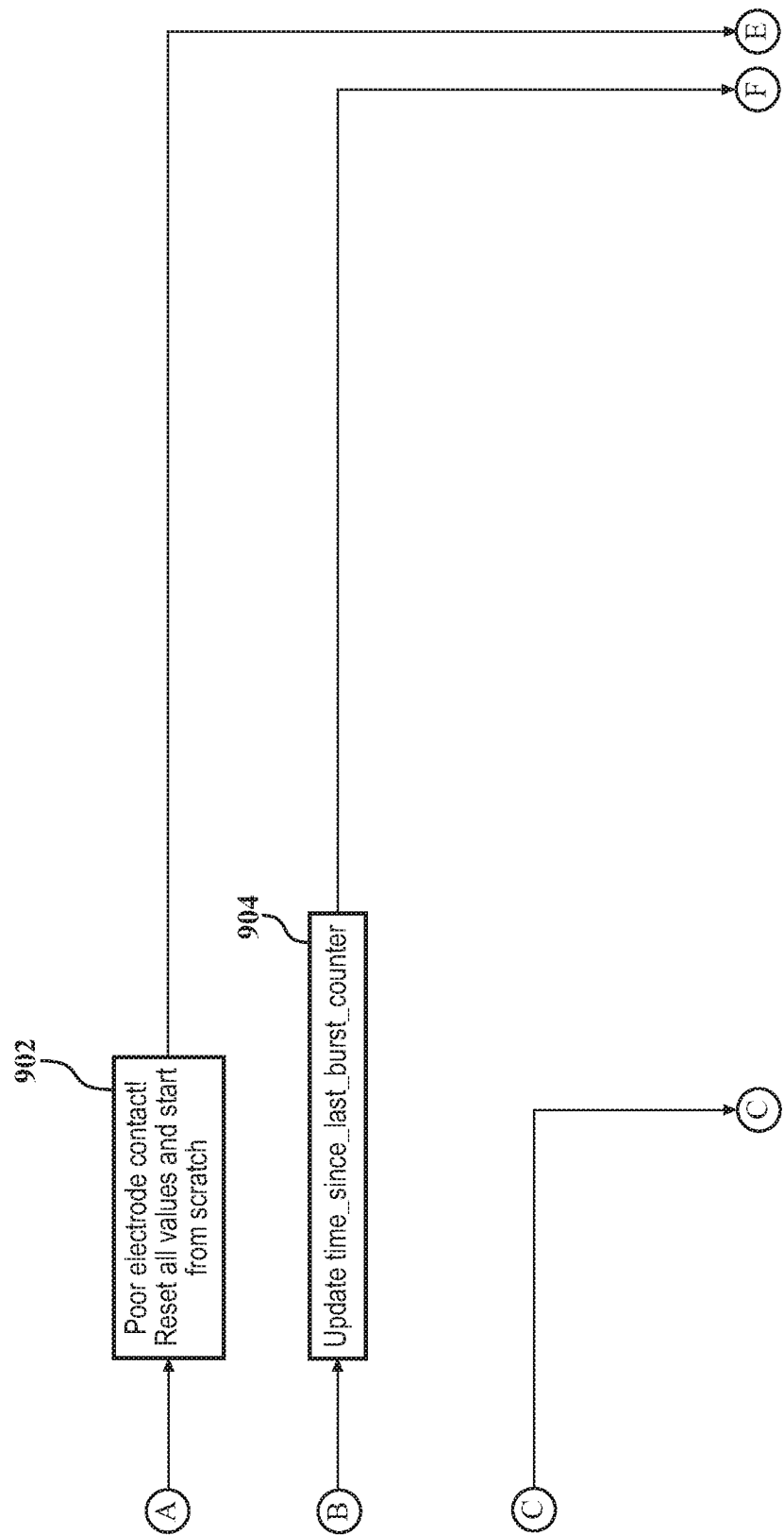

AUTOMATIC DETECTION OF TEETH CLENCHING AND/OR TEETH GRINDING

FIELD OF INVENTION

The present disclosure relates to automatic detection of a predefined event in a dataset, more specifically to a method, a device and a system for automatic detection of teeth clenching and/or teeth grinding.

BACKGROUND OF INVENTION

In a number of circumstances it is desirable to detect teeth clenching and/or teeth grinding of especially human beings, in particular with the objective of being able to detect and possibly avoid undesirable, unnecessary and/or potentially harmful teeth clenching and/or grinding. In particular it is desirable to be able to detect such teeth clenching and/or grinding with the objective of being able to interfere in such a manner that the undesirable activity may be limited or even brought to an end.

Teeth clenching and/or teeth grinding may be done more or less consciously or even completely unaware, for example in the sleep, and may also cause damage or unwanted effects.

Both teeth clenching and teeth grinding may be categorized as the affliction known as bruxism; powerful jaw movements without any real function which takes the form of involuntary grinding movements of the teeth during strong clenching. This affliction may cause serious dental damages such as for example wearing of the teeth, damages to lips and the tongue, lose teeth, gingival pockets etc. Bruxism is often in addition also associated with pain in the back of the head and chronic headache.

Bruxism is normally divided into chronic and acute bruxism. Acute bruxism can happen to all and may often be observed in stress situations, for example at athletes in games or at persons that have to observe a deadline. Chronic bruxism is divided into night-time (nocturnal) and day-time (diurnal) bruxism.

Day-time bruxism is characterized by being a conscious clenching of upper and lower jaws and grinding of the teeth, although dominated by the latter. Day-time bruxism may be perceived as a bad habit. Triggering of day-time bruxism may be related to exposing a patient to stress. Day-time bruxism may be relieved relatively easy by informing the person that he/she is bruxing.

Night-time bruxism is unconscious and may normally only be perceived by the surroundings (for example relations) as an unpleasant squeaky noise. During night-time bruxism, teeth grinding is more common than teeth clenching. Night-time bruxism is often alleviated by protecting the teeth with a splint.

Using monitoring devices, it is possible to detect events related to bruxism. However, events related to bruxism may be difficult to detect because they may be similar to event related to ordinary teeth clenching. On the other hand, both day and night time bruxism typically lasts more than 2-5 seconds. This knowledge may be used to detect events directly related to bruxism and so it has been. Several monitoring devices exist to monitor events related to bruxism, for example by sensing signals from muscular activity of the jaw such as electrical signals or sound signals. In common for these devices is that they require a patient or another person to manually set up the devices such that they become adapted to the individuals, in particular such that the devices sense the signals related to jaw movements and distinguish them from other signals as given off by the individuals.

An example of a device with an automatic threshold to discriminate between normal jaw movement and muscular activity related to bruxism based on a manual setup is disclosed in WO04087258 A1.

A manual set up is far from optimal in that the sensing device may then depend on the person setting up the device. If the detected signals may be used, as for example by providing a treatment stimulus to the patient, an incorrect set up may be problematic in that a correct treatment may not be provided.

SUMMARY OF INVENTION

In order to solve the above described problems and address the above described needs, the present disclosure relates to a user-friendly device which automatically detects teeth clenching and/or teeth grinding without the use of a manual set up. The user friendly device may be easy to use in terms of daily setup, such that particularly calibration is avoided. Accordingly, the present disclosure relates to a user-friendly method which automatically set up a device such that it becomes adapted to the individuals, in particular such that the device detects the teeth clenching and teeth grinding signal and distinguish them from other signals as given off by the individuals.

Accordingly, the present disclosure provides a computer implemented method for automatic detection of teeth clenching and/or teeth grinding in a dataset representing the level of biting force vs. time of a subject, the method comprising the steps of a) calculating a threshold level of biting force assigned to time $t=t_1$ based on a background level determined from the dataset at a prior time $t=t_1-T_{back}$, where $T_{back}$ is a first predefined period of time, b) checking the level of biting, and if the level of biting force at time, t, exceeds the threshold level assigned to time $t_1$ for a second predefined period of time, $T_{clench/grind}$, then assigning an event of teeth clenching to time t, c) if an event of teeth clenching has been assigned to time t, then either waiting a predefined period of time $T_{wait}$, or waiting until the level of biting is below the threshold for another predefined period of time $T_{end}$, d) if no events of teeth clenching and/or teeth grinding have been assigned for a third predefined period of time $T_{silence}$, then repeating steps a)-c), e) if events of teeth clenching and/or teeth grinding have been assigned for a third predefined period of time $T_{silence}$, then repeating only steps b)-c).

The presently disclosed method is based on the principle that the threshold level constantly adapts to and is delayed from the background level. This may find use in broader aspect than detection of teeth clenching and/or teeth grinding. In a more general aspect the present disclosure therefore relates to a computer implemented method for automatic detection of a predefined event in a dataset representing the level of muscular activity vs. time of a subject, the method comprising the steps of:

a) calculating a threshold level of muscular activity assigned to time $t=t_1$ based on a background level determined from the dataset at a prior time $t=t_1-T_{back}$, where $T_{back}$ is a first predefined period of time, b) checking the level of muscular activity, and if the level of muscular activity at time, t, exceeds the threshold level assigned to time $t_1$ for a second predefined period of time, $T_{clench/grind}$, then assigning an event to time t, c) if an event has been assigned to time t, then either waiting a predefined period of time $T_{wait}$, or waiting until the level of muscular activity is below the threshold for another predefined period of time $T_{end}$, d) if no events have been assigned for a third predefined period of time $T_{silence}$, then repeating steps a)-c), e) if events have been assigned for a third predefined period of time $T_{silence}$, then repeating only steps b)-c).

One purpose of the presently disclosed method is to determine the background level when there are no muscle events related to teeth clenching and/or teeth grinding. Since both day and night time bruxism typically lasts more than a few seconds and with an onset that is abrupt, then the background level, as determined from a period of time longer than the event related to bruxism, may not be affected by the event related to bruxism. Furthermore, if more than a predefined time has passed since the end of the latest burst of an event related to bruxism, it is most likely that the signal may contain no events related to bruxism, and therefore it may be a good estimate of the background level. Thus a pseudo-code of the method may be written as follows:

```
{
    calculate envelope of signal
    check for signal activity (burst and/or grind active?)
    if there is no current activity AND no activity has appeared for a
    predefined period,
    then
    {
        calculate new background value based on signal envelope level
        another predefined time ago
    }
}
```

According to described method, it is one purpose of the present disclosure to assign an event to teeth clenching and/or teeth grinding.

Furthermore, the present disclosure provides a data-processing system comprising a processor and a memory which may be configured to perform the method as described above.

Also, the present disclosure provides a device for monitoring facial activity related to teeth clenching and/or grinding of a subject comprising a measuring unit for providing signals indicative of said facial activity, and a processing unit for processing said signals in order to detect said teeth clenching and/or teeth grinding.

Due to the desire of a user friendly device and/system, the present disclosure further relates to a bruxism system comprising the above described device and a storage case for housing and charging the device, wherein the device is configured to be automatically switched on when removed from the storage case. Furthermore, the present disclosure relates to a user-friendly device which automatically turns on when it is placed on the user, and also turns of when not on the user.

DESCRIPTION OF FIGURES

FIGS. 9A and 9B show embodiment of the disclosed method illustrated as a part of the flow chart from FIG. 7.

DETAILED DESCRIPTION OF THE INVENTION

Teeth Clenching and/or Teeth Grinding

Figure 1:
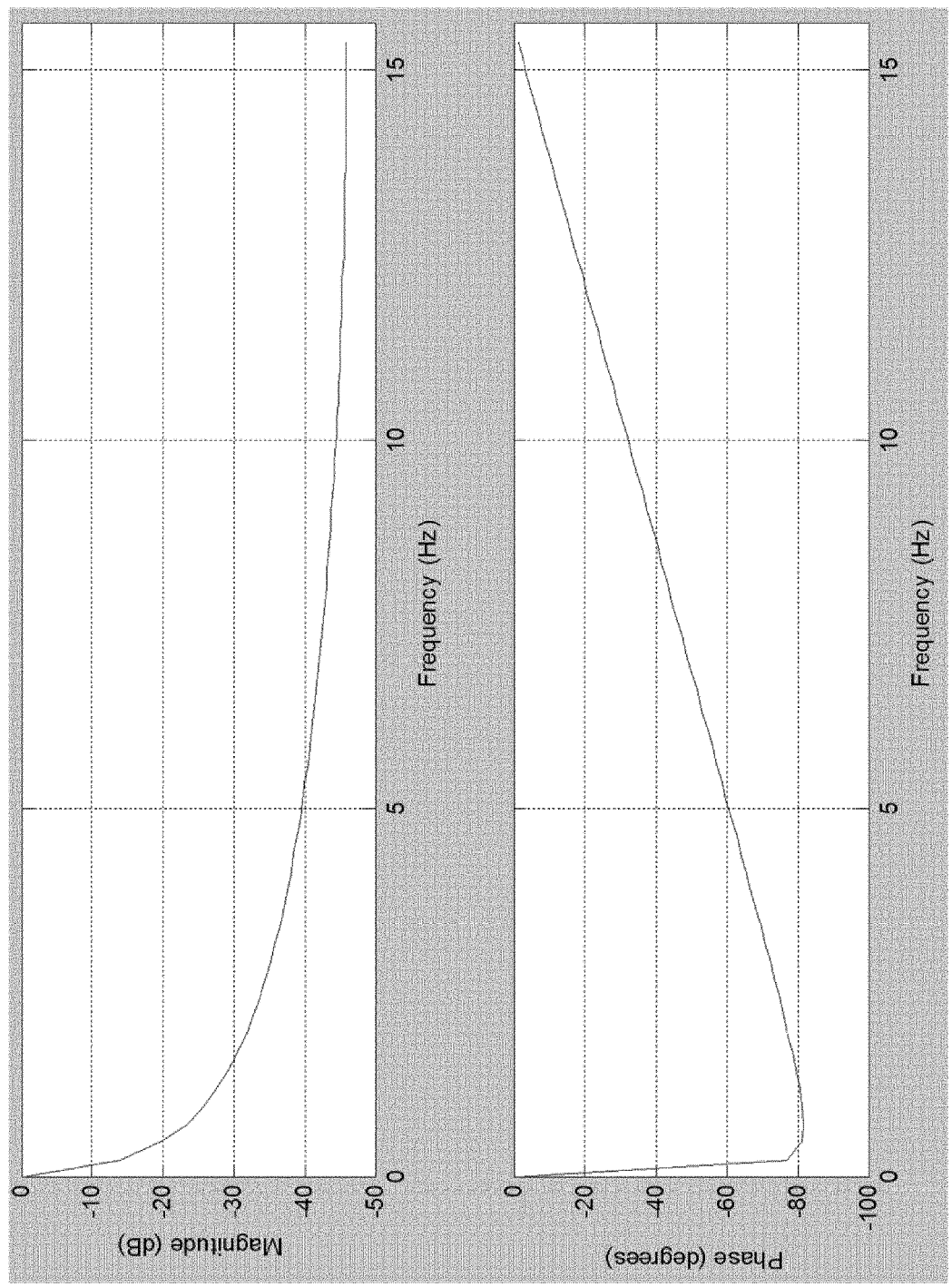
FIG. 1 shows a magnitude and phase plot of an embodiment a $1^{st}$ order lowpass filter.

An event of teeth clenching and/or teeth grinding may be characterized as one or more of the following: bruxism, day-time bruxism, night-time bruxism.

Teeth grinding is when people slide their teeth back and forth over each other, whereas teeth clenching is when people tightly hold their top and bottom teeth together. In this way, the two terms are per se different events. However, both events are related to muscular activity of the jaw. The medical term for both teeth grinding and teeth clenching is bruxism.

As described, bruxism can be chronic and acute, whereof chronic bruxism can be night-time (nocturnal) bruxism and day-time (diurnal) bruxism.

Signals

Since teeth clenching and teeth grinding is related to muscular activity of the jaw, it may be advantageous to have a dataset from a signal to represent muscular activity of the jaw vs. time of the subject. Accordingly, the dataset may comprise electromyography (EMG) data from EMG signals.

EMG signals are electrical impulses of muscles, which may be measured at rest and during contraction. An EMG signal is small and needs to be amplified with an amplifier that is specifically designed to measure physiological signals. This signal may be measured with an electrode. A skin surface electrode may often be preferred, because it is placed directly on the skin surface above or near the muscle.

The point of interest of the signal is the amplitude, which may range between 0 to 10 millivolts (peak-to-peak) or 0 to 1.5 millivolts (root-mean-square). The frequency of an EMG signal may be between 0 to 500 Hz. However, the usable energy of EMG signal may be dominant between 50-150 Hz.

As regards EMG-signals, focus will be placed on the chewing muscles when teeth clenching and/or teeth grinding is involved. In technical language, these muscles are called muscle Temporalis and muscle Masseter, which can be utilised for the registration of EMG signals in connection with teeth clenching and/or teeth grinding.

The Masseter muscle consists of two parts, a surface muscle and a deeper-lying part which, while strongly clenching the teeth, can easily be localised by pressing a finger into the cheek and leading it out from the mouth towards the ear. The main task of the Masseter muscle is to raise the lower jaw, although it also plays a part in the lower jaw's horizontal movement (as a part of the chewing movement). It contributes towards drawing the lower jaw forwards. Muscle Temporalis is a large fan-shaped muscle which covers and adheres to a large part of the side of the cranium, which means that most of it is freely accessible.

Movements of the jaw may give rise to various bio-signals that may be measured. The presently disclosed method may work regardless of the signals. Thus, it may be possible to automatically detect the background level regardless of the signal, such that the background signal can be used to automatically determine a threshold level without a calibration procedure. In this regard, it is one purpose of the present disclosure to provide a method that operates on any type of signal and thereby provide a user-friendly setup, i.e. an automatic setup, meaning no manual setup, regardless of the signals.

Accordingly, signals other than EMG signal may be used to represent muscular activity of the jaw. Hence the dataset may comprise one or more of the following: electromyography (EMG) data, electroencephalography (EEG) data, phonomyography (PMG) data, acceleration data, sound data and/or strain gauge data.

These data may accordingly be obtained from EMG signals, EEG signals, PMG signals, acceleration signals, sound signals and/or strain gauge signals.

EEG signals are electric fields of the human brain. Accordingly, EEG may be measured on the scalp or on the brain. The amplitude of the EEG may be about 100 µV when measured on the scalp, and about 1-2 mV when measured on the surface of the brain. The bandwidth of this signal may be from under 1 Hz to about 50 Hz. EEG signals are closely related to the level of consciousness of the person. As the activity increases, the EEG shifts to higher dominating frequency and lower amplitude. Thus, muscular activity may be observed using EEG signal.

PMG signals are the low frequency sounds created during muscular activity. It may therefore be possible to measure the force of muscle contraction from PMG signals. PMG signals may be from 1 Hz to 100 Hz.

Acceleration signals may be voltages created when a muscle accelerates. Hence, acceleration signals may be measuring muscle activity using an accelerometer, such as a miniature piezoelectric transducer by attaching it to the stimulated muscle. Accelerometers may be a pair of microstructures next to each other such that they detect the changes in their capacitance; by converting the change in capacitance to a change in voltage, the acceleration may be obtained. Accelerometers may also be use the piezo-resistive effect, hot air bubbles, and light.

Sound signals may be the sounds produced by for example the teeth during events of teeth grinding, and may accordingly be recorded using a microphone. Clenching may not produce sounds, and in this way, it may be possible to distinguish between teeth grinding and teeth clenching.

Strain gauge signals are changes in resistance corresponding to strain, and may be a way to measure movement of the jaw. Strain may be measured using a strain gauge, for example in the ear.

The signals generating the dataset may be a stream of data continuously received from a measuring unit.

Regardless of the signals, it is one purpose of the present disclosure to relate any of the described signals for detection events related to teeth clenching and/or teeth grinding, thereby allowing one or more of the signals to be used in the detection. In other words, it is an objective or the present disclosure to provide some kind of pattern recognition, which may be applied to any signal in order to detect events related to teeth clenching and/or teeth grinding. It must be noted, that teeth clenching and/or teeth grinding may not need to be related to bruxism.

Background Level and Threshold Level

In one embodiment of the present disclosure, the background level is determined by applying a low-pass filter to the dataset. In this way, the background level may be a smoothed signal containing only low frequency components. The low pass filter may in particular be a first order filter with a cut-off frequency of for example 0.05 Hz. In some embodiments of the present disclosure, the background signal may be determined by applying another type of filter to the data set, such as a bandpass filter or a high-pass filter. The background level may be an estimate of the noise level, where the noise may be thermal noise from an electrode, amplifier noise and/or external noise. Accordingly, the background level may be the level of a recorded signal in the absence of muscle activity. The background level may depend on the impedance of the electrode. Thus, the background level may be dependent on the placement of electrodes, in that electrodes may be placed on skin, for example using gelpads, where for example moist will be created, and this may affect the impedance. In this regard, there may be circumstances, where the background level may be time-dependent. It is with this in mind, that the background level may be determined at different times during use.

In a preferred embodiment of the present disclosure, the threshold level may be greater than and proportional to the background level. Accordingly, the threshold value may be defined to be at least 1.5, 2, 3, 4 or at least 5 times the background level.

Signal Processing

In order to process the signals, it may be required to include an initial step of providing a frequency domain transform of the dataset, a frequency domain transform such as fast Fourier transform (FFT), discrete Fourier transform (DFT), discrete cosine transform (DCT) or discrete wavelet transform (DWT).

The frequency domain may in some embodiments be more preferred than the time domain, in that for example frequency filtering, such as low pass filtering, may be more easily implemented. Other advantages, such as reduced calculation time, may also be obtained by working in the frequency domain. Furthermore, by applying a DWT, advantages are that transient features are accurately captured and localized in both time and frequency. In relation to this, some special DWTs may increase computational speed of for example algorithms in comparison to applying for example Fourier transforms or classical DWTs.

According to the initial step, it may comprise the step of averaging a predefined number of frequencies. A predefined number may be advantageous over for example an estimated number in that the estimation may be avoided. Thus, the predefined number may be used to speed up the calculation time.

As an example of a signal processing, a signal envelope may be calculated from the result of the applied FFT for each block of raw signal values. The signal may be sampled at a rate of 2000 samples/s and blocks of 64 samples may be collected for FFT analysis. This results in a sample rate of 31.25 samples/s for the signal envelope. For each block of data, the FFT may be applied, and the result may be represented as 32 'pins' of data, where each pin represents a step of 31.25 Hz. The pin value may be the amplitude of the frequency spectrum at the specific frequency. The 0-pin may contain the DC value. The signal envelope may be obtained by the mean value of pin 7-13, where pins 7-13 represents values from 218.75 Hz to 406.25 Hz.

Figure 4A:
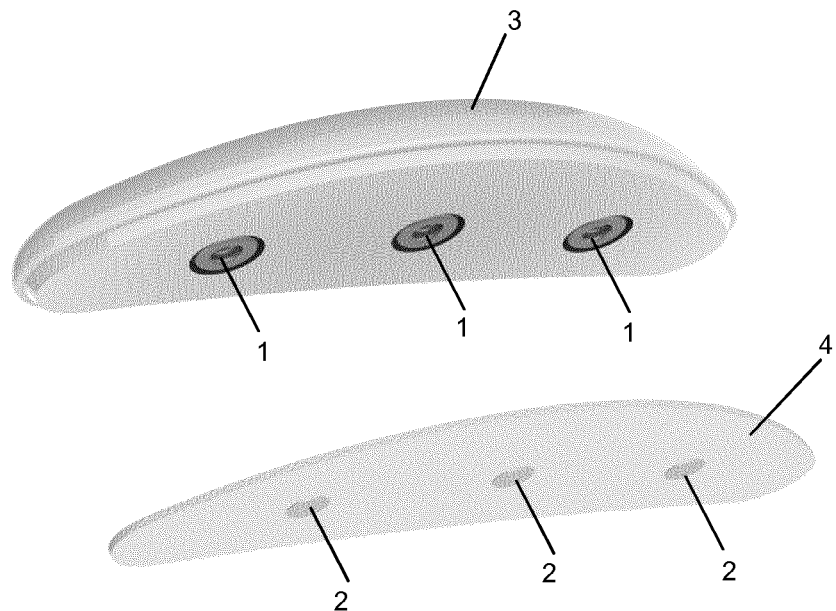
FIG. 4 shows an embodiment of a measuring unit.
Figure 4B:
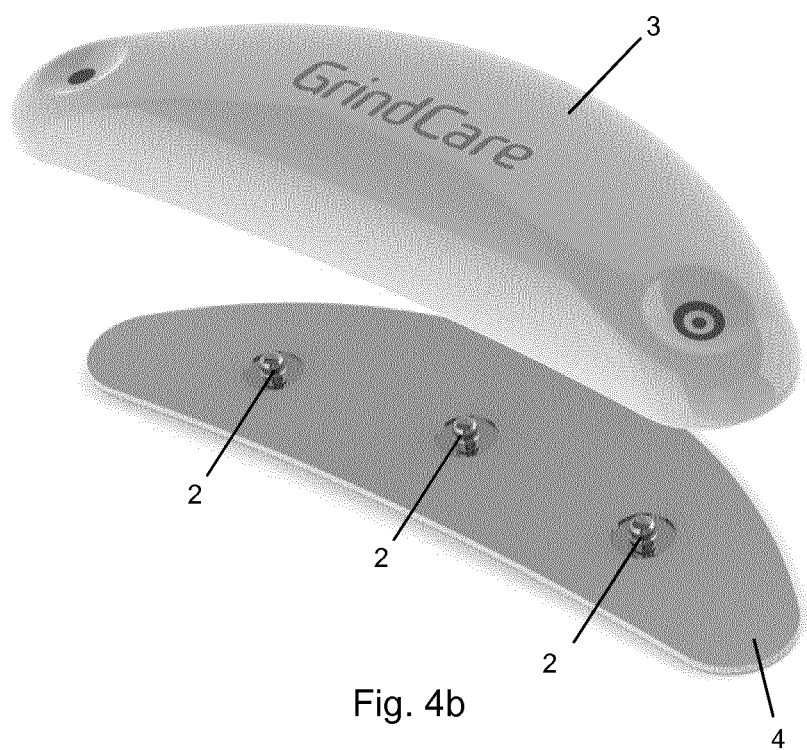

Since the calculation time may be fast, the automatic detection of teeth clenching and/or teeth grinding may be a real-time process carried out on a stream of data continuously received. Accordingly, the data may not need to be stored, and therefore the processing unit may be integrated in the measuring unit and still be as compact as shown in FIG. 4.

Predefined Time Periods

In a preferred embodiment of the disclosure, the times $T_{end}$, $T_{clench/grind}$, $T_{back}$, $T_{silence}$, are predefined time periods, meaning time parameters, defined such that $T_{end} \leq T_{clench/grind} < T_{back} < T_{silence}$.

$T_{end}$:

$T_{clench/grind}$ may be regarded as a predefined time period in which events related to teeth clenching and/or teeth grinding is ending. Accordingly, $T_{end}$ may in a preferred embodiment of the present disclosure be 0.125 s, or less than 0.25 s, or less than 0.5 s, or less than 0.4 s, or less than 0.35 s, or less than 0.3 s, or less than 0.25 s, or less than 0.2 s, or less than 0.15 s, or less than 0.1 s, or less than 0.05 s, or less than or less than 0.01 s.

$T_{clench/grind}$:

$T_{clench/grind}$ may be regarded as a predefined time period in which events related to teeth clenching and/or teeth grinding is at least to last. In this way, all events less than $T_{clench/grind}$ may not be related to teeth clenching and/or teeth grinding. Events that last less than $T_{clench/grind}$ may be a normal bite or any normal movement of the jaw. Accordingly, $T_{clench/grind}$ may in a preferred embodiment of the present disclosure be 0.25 s, or less than 0.5 s, or less than 0.4 s, or less than 0.35 s, or less than 0.3 s, or less than 0.25 s, or less than 0.2 s, or less than 0.15 s, or less than 0.1 s, or less than 0.05 s.

$T_{back}$:

$T_{back}$ may be regarded as a predefined time period in which the background level is recorded. Accordingly, $T_{back}$ may in a preferred embodiment of the present disclosure be 2.5 s, or less than 10 s, or less than 8 s, or less than 6 s, or less than 5 s, or less than 4 s, or less than 3 s, or less than 2 s, or less than 1 s. Accordingly, $T_{back}$ may in another preferred embodiment of the present disclosure be at least 2.5 s, or at least 1 s, or at least 2 s, or at least 3 s, or at least 4 s, or at least 5 s, or at least 6 s, or at least 7 s, or at least 8 s, or at least 9 s, or at least 10 s.

$T_{silence}$:

$T_{silence}$ may be regarded as a predefined time period in which there may be no events related to teeth clenching and/or teeth grinding, before an initiating of a repeated procedure takes place. Since there may be no events related to teeth clenching and/or teeth grinding in the time period $T_{silence}$, there may be silent. Accordingly, $T_{silence}$ may in a preferred embodiment of the present disclosure be 5 s, or less than 10 s, or less than 8 s, or less than 6 s, or less than 5 s, or less than 4 s, or less than 3 s, or less than 2 s, or less than 1 s. Accordingly, $T_{silence}$ may in another preferred embodiment of the present disclosure be at least 5 s, or at least 1 s, or at least 2 s, or at least 3 s, or at least 4 s, or at least 5 s, or at least 6 s, or at least 7 s, or at least 8 s, or at least 9 s, or at least 10 s.

$T_{wait}$:

$T_{wait}$ may be regarded as a predefined time period in which the measuring unit may be configured to stop providing signal indicative of facial activity when a feedback signal is providing in response to detecting bruxism. Accordingly, $T_{wait}$ may in a preferred embodiment be 1 s, or less than 10 s, or less than 8 s, or less than 6 s, or less than 5 s, or less than 4 s, or less than 3 s, or less than 2 s, or less than 1 s. In another preferred embodiment of the present disclosure, $T_{wait}$ may at least be 1 s, or at least 1 s, or at least 2 s, or at least 3 s, or at least 4 s, or at least 6 s, or at least 7 s, or at least 8 s, or at least 9 s, or at least 10 s.

Further, $T_{end}$ may be between 0.4 and 0.6 times $T_{clench/grind}$ or $T_{end}$ may be between 0.3 and 0.7 times $T_{clench/grind}$ or $T_{end}$ may be between 0.45 and 0.55 times $T_{clench/grind}$ or wherein $T_{end}$ may be 0.5 times $T_{clench/grind}$.

Further, $T_{back}$ may be between 0.4 and 0.6 times $T_{silence}$ or between 0.3 and 0.7 times $T_{silence}$ or between 0.45 and 0.55 times $T_{silence}$ or $T_{back}$ may be 0.5 times $T_{silence}$.

Further, $T_{clench/grind}$ may be between 0.05 and 0.15 times $T_{back}$ or between 0.02 and 0.25 times $T_{back}$ or between 0.08 and 0.12 times $T_{back}$ or $T_{clench/grind}$ may be 0.1 times $T_{back}$.

Further, $T_{wait}$ may be less than $T_{back}$ and less than $T_{silence}$, such as between 0.15 and 0.25 times $T_{silence}$ or $T_{wait}$ may be 0.1 times $T_{silence}$.

Processing Unit

In a preferred embodiment of the present disclosure, the processing unit is configured to automatically determine a threshold level according to previously described.

Accordingly, the processing unit may be configured to perform the previously described method such that it may be used for automatic detection of teeth clenching and/or teeth grinding.

In the presently disclosed method, the frequency domain transform is hardware implemented in the processing unit. This may be advantageous in that it may speed up the processing time.

Furthermore, in the presently disclosed method, the signals indicative of said facial activity represents the level of biting force vs. time of the subject and wherein the processing unit is configured to perform the described method and wherein an event of teeth clenching and/or teeth grinding is an event of bruxism. As previously described, the various signals may be related to the facial activity such as moving the jaw, thereby able to represent the level of biting force vs. time and relate this to bruxism. The facial activity may also be muscle activity, teeth grinding, and/or teeth clenching.

Measuring Unit

In one embodiment of the present disclosure, the measuring unit comprises at least one electrode assembly for providing said signals. The signals as previously described are indeed measurable using at least one electrode.

Feedback Unit

In one embodiment of the present disclosure, the device is further comprising a feedback unit for providing a feedback signal in response to detecting said bruxism. In this way, the feedback unit may be able to provide treatment of bruxism. If the feedback may be provided for night-time bruxism, the feedback may be such that the user may not be awakened during sleep. Furthermore, the feedback may not be given in situations that are not related to bruxism.

Accordingly, the measuring unit may be configured to provide a feedback signal in response to detecting said bruxism. The feedback signal may be a visual, tactile, acoustic, and/or medical, such as a relaxing agent, feedback delivered to the subject. In the case of a visual feedback signal, it may for example be on a screen, such as on a smartphone, a phone, a tablet, a computer screen or any type of display. The visual feedback may however also be a diode, such as an LED, or any type of lamp. In the case of tactile feedback signal, it may for example be a vibration such as from vibrators in smartphones or phones. The accoustic feedback signal may be a sound from a speaker such as within a smartphone, a phone or a speaker by itself.

In another embodiment of the present disclosure, the measuring unit is configured to stop providing signals indicative of facial activity for a predetermined period of time, when a feedback signal is provided in response to detecting said bruxism. This may be to avoid too many signals at the same time.

Design and Power Integration

In one embodiment of the present disclosure, the processing unit is integrated/incorporated in the measuring unit. Such a design may allow the user to wear only one unit. Accordingly, the device may be manufactured with low cost such as in terms of materials.

In another embodiment of the present disclosure, the measuring unit comprises an electrode assembly configured to be attached to the skin of the subject and wherein the device is configured to monitor the electrical connection between the electrode assembly and the skin, and wherein the processing unit is configured to begin processing the signals when a connection between skin and electrode assembly has been detected. Such a configuration may allow for optimal power usage, i.e. to save power and provide user-friendly operation. In this regard, the device may be further comprising an internal chargeable electrical power source, such as a battery, for powering the device.

User-Friendly Bruxism System

In one embodiment of the present disclosure, the device and the storage case are configured such that the device is automatically switched off when installed in the storage case if the storage case is not connected to an external electrical power source. Such a configuration may allow for optimal power usage, i.e. to save power and provide user-friendly operation.

According to one embodiment of the present disclosure, the storage case may comprise an electrical circuit configured to detect an electrical connection between the storage case and the device. Accordingly, the device may comprise at least one magnet and the storage case may comprise a sensor unit for sensing the presence of a magnetic field, such as a hall-effect switch, and wherein the storage case sensor is configured to detect the presence of the device in the storage case.

In another embodiment of the present disclosure, the device may comprise a mechanical switch that is configured to be engaged by the device when the device is installed in the storage case.

In yet another embodiment of the present disclosure, the storage case and the device is configured such that the internal chargeable electrical power source in the device is charged by electrical power transmitted wirelessly from the storage case to the device. This may ease operation of the device.

EXAMPLE 1

In order to calculate a background level, the background level may be a low pass filtered EMG signal envelope as here described.

The filter is a $1^{st}$-order autoregressive filter in the form:

$$y(n)=0.99 \cdot y(n-1)+0.01 \cdot x(n-80), \text{ where}$$

$x(n-80)$ is the 2.56 second old envelope value (80 samples/31.25 samples/s=2.56 s),
$y(n-1)$ is the latest value of the background level,
$y(n)$ is the new value of the background level,
0.99 is the filter coefficient,
0.01 is a gain-factor on the input signal, to ensure an overall gain of 1.

The calculation is implemented in integer arithmetic, to reduce computational load in the embedded processor. This is done by multiplying the values from the FFT algorithm (which is an 8-bit algorithm), with a scaling factor of 10000. Further, the filter described above is calculated as $$y(n)=(99 \cdot y(n-1)+1 \cdot x(n-80))/100$$

as decimal numbers cannot be represented in integer arithmetic.

The Magnitude and Phase responses of the filter are shown in FIG. 1. It has a −3 dB cutoff frequency of 0.05 Hz (1/20 Hz).

EXAMPLE 2

Figure 2:
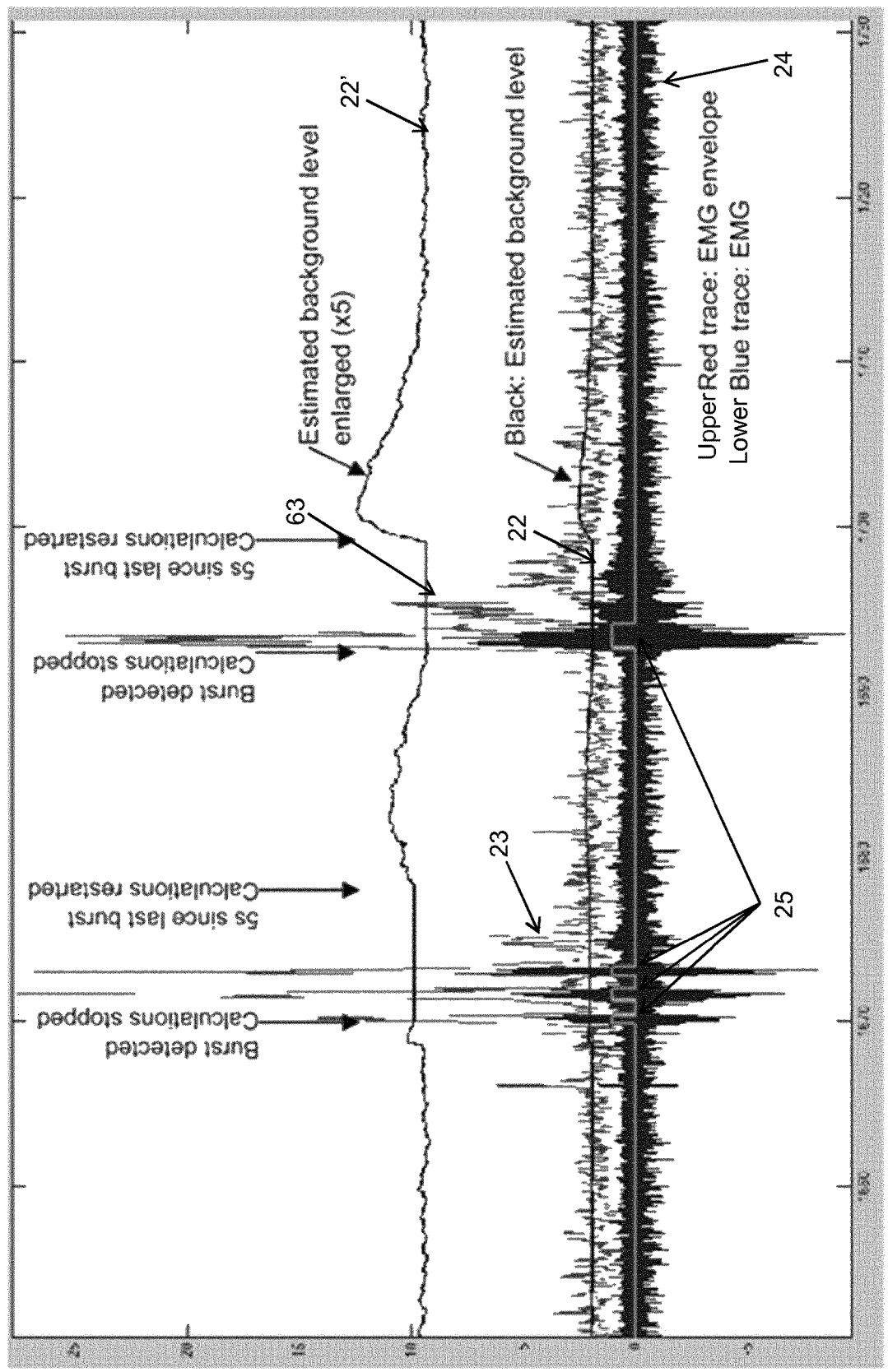
FIG. 2 shows an embodiment of the disclosed method.

An illustration of an embodiment of the method for automatic detection of teeth clenching is shown in FIG. 2. In FIG. 2, the data is EMG data obtained from EMG signals. The signal envelope 23 is calculated by FFT of the raw EMG signal 24. As can be seen from FIG. 2, the estimated background level 22, 22' is constantly changing with respect to time, except for the periods wherein the calculation is stopped, i.e. wherein the method is fixing the threshold level, and after which the calculations are restarted. It can be seen in FIG. 2 that four bursts 25 are detected in total.

EXAMPLE 3

Figure 3:
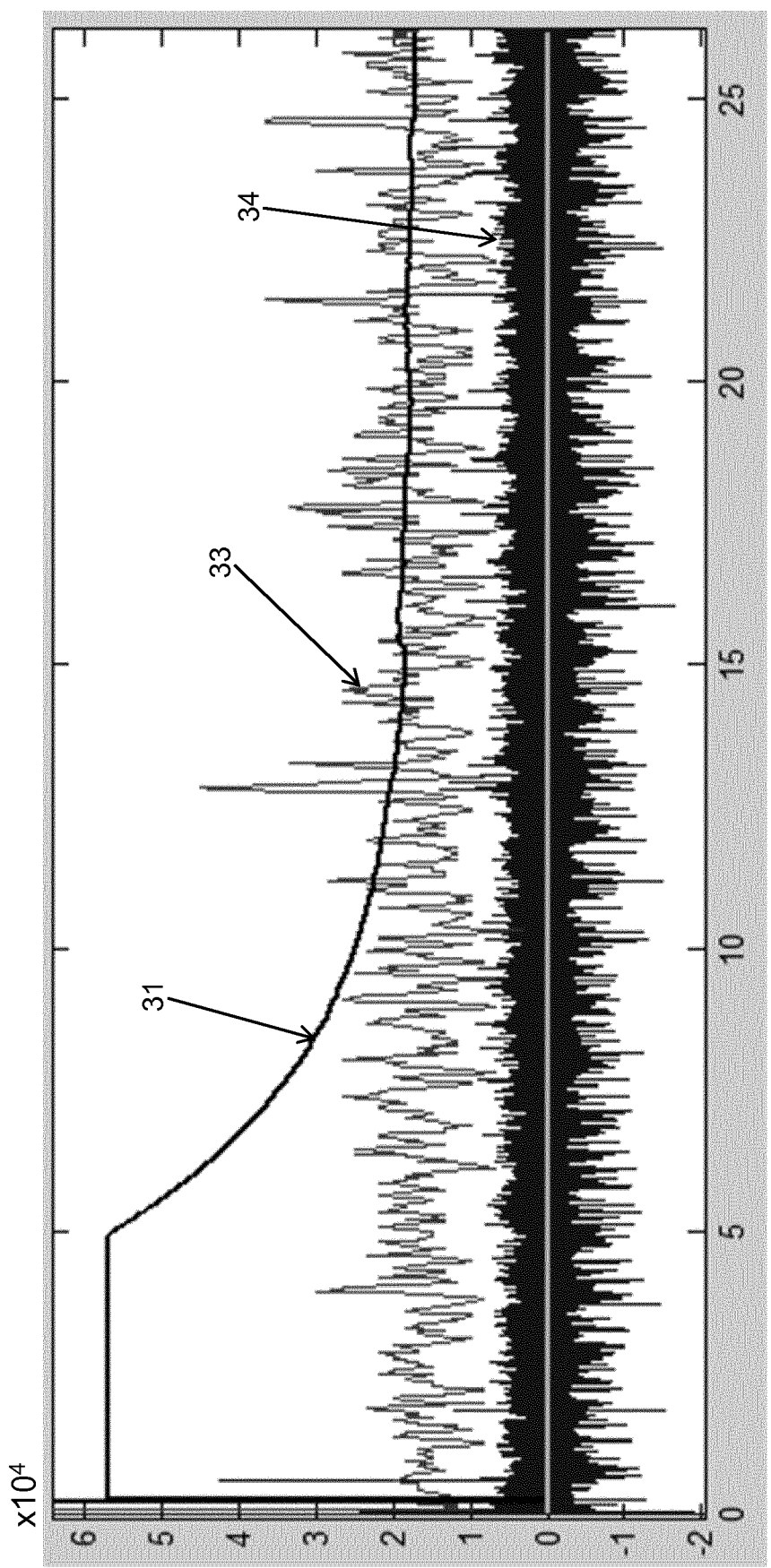
FIG. 3 shows another embodiment of the disclosed method.

An illustration of another embodiment of the method for automatic detection of teeth clenching is shown in FIG. 3. In FIG. 3, the data is EMG data obtained from EMG signals. In FIG. 3 is shown the initial output from the method when no activity related to the teeth clenching has been assigned. The raw EMG signal 34 is sampled at 2000 Hz. The signal envelope 33 is calculated by a 64-point FFT and averaging pins 7-13, as this corresponds to an RMS value of frequencies between 218 and 406 Hz. As can be seen from FIG. 3 the initial output of the background level 31 is rather high and the method waits 5 seconds before it starts calculating new outputs (assuming that a signal may have been present before the start of the method). The initial value of the background level 31 is set to a higher value than expected in the recorded signal 34. Due to the high start level and depending on the actual level of background activity, it can take up to 10 s for the filter to find the precise level of the background activity. In this particular example, the filter has a time constant, $\tau=1/(2\pi f_{3dB})$ where $f_{3dB}=0.05$ Hz, i.e. $\tau=3.2$ s.

EXAMPLE 4

An example of a measuring unit is shown in FIG. 4. It comprises three electrode assemblies, each assembly consisting of an electrode connector 1, an electrode 2 to be connected on the top surface 3, such that the bottom surface 4, connects to the skin with the three electrodes 2.

EXAMPLE 5

Figure 5:
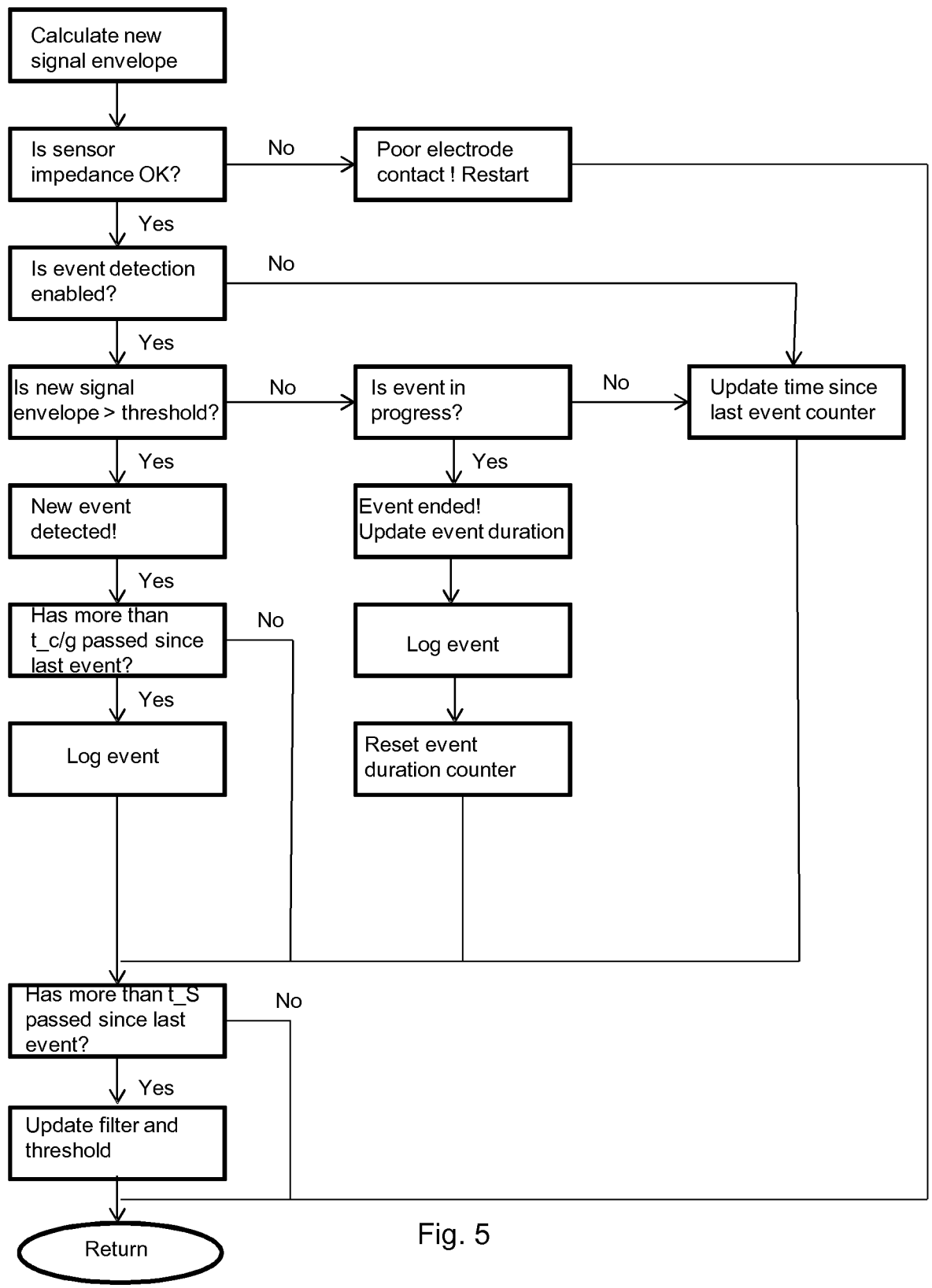
FIG. 5 shows an embodiment of the disclosed method illustrated as a flow chart.

Another embodiment of the method for automatic detection of teeth clenching, illustrated as a flow chart, is shown in FIG. 5. The flow chart starts from the top, where a new signal envelope is calculated. This is an initial step to the disclosed method, which may be providing a frequency domain transform of the dataset, a frequency domain transform such as fast Fourier transform (FFT), discrete Fourier transform (DFT), discrete cosine transform (DCT) or discrete wavelet transform (DWT). The initial step as here illustrated may also comprise the step of averaging a predefined number of frequencies. The next step may be related to the measuring unit, since the measuring unit may comprise an electrode assembly configured to be attached to the skin of the subject and wherein the device may be configured to monitor the electrical connection between the electrode assembly and the skin, and wherein the processing unit may be configured to begin processing the signals when a connection between skin and electrode assembly has been detected. In case of poor electrical connection between the electrode assembly and the skin, the measuring unit restarts as shown in the flow chart. When beginning processing the signals, it may also check whether or not event detection is enabled as also shown in flow chart. In case of event detection being disabled, the time since last event is being updated as shown in the flow chart. From here, and in all circumstances, if no events of teeth clenching and/or teeth grinding has been assigned for a third predefined period of time $T_{silence}$, it may be possible to go back to start. In some cases, the step back to start may be followed with a calculation of a threshold level of biting force assigned to time $t=t_1$ based on a background level determined from the dataset at a prior time $t=t_1-T_{back}$, where $T_{back}$ is a first predefined period of time. From start, there may be a check of the level of biting, and if the level of biting force at time, t, exceeds the threshold level assigned to time $t_1$ for a second predefined period of time, $T_{clench/grind}$, then there may be assigned an event of teeth clenching to time t. If an event of teeth clenching has been assigned to time t, then there may be either a waiting of a predefined period of time $T_{wait}$, or a waiting until the level of biting is below the threshold for another predefined period of time $T_{end}$. If no events of teeth clenching and/or teeth grinding have been assigned for a third predefined period of time $T_{silence}$, the procedure repeats itself. On the other hand, if events of teeth clenching and/or teeth grinding have been assigned for a third predefined period of time $T_{silence}$, then there may be a repeating of only some of the steps as shown in the flow chart.

EXAMPLE 6

Figure 6:
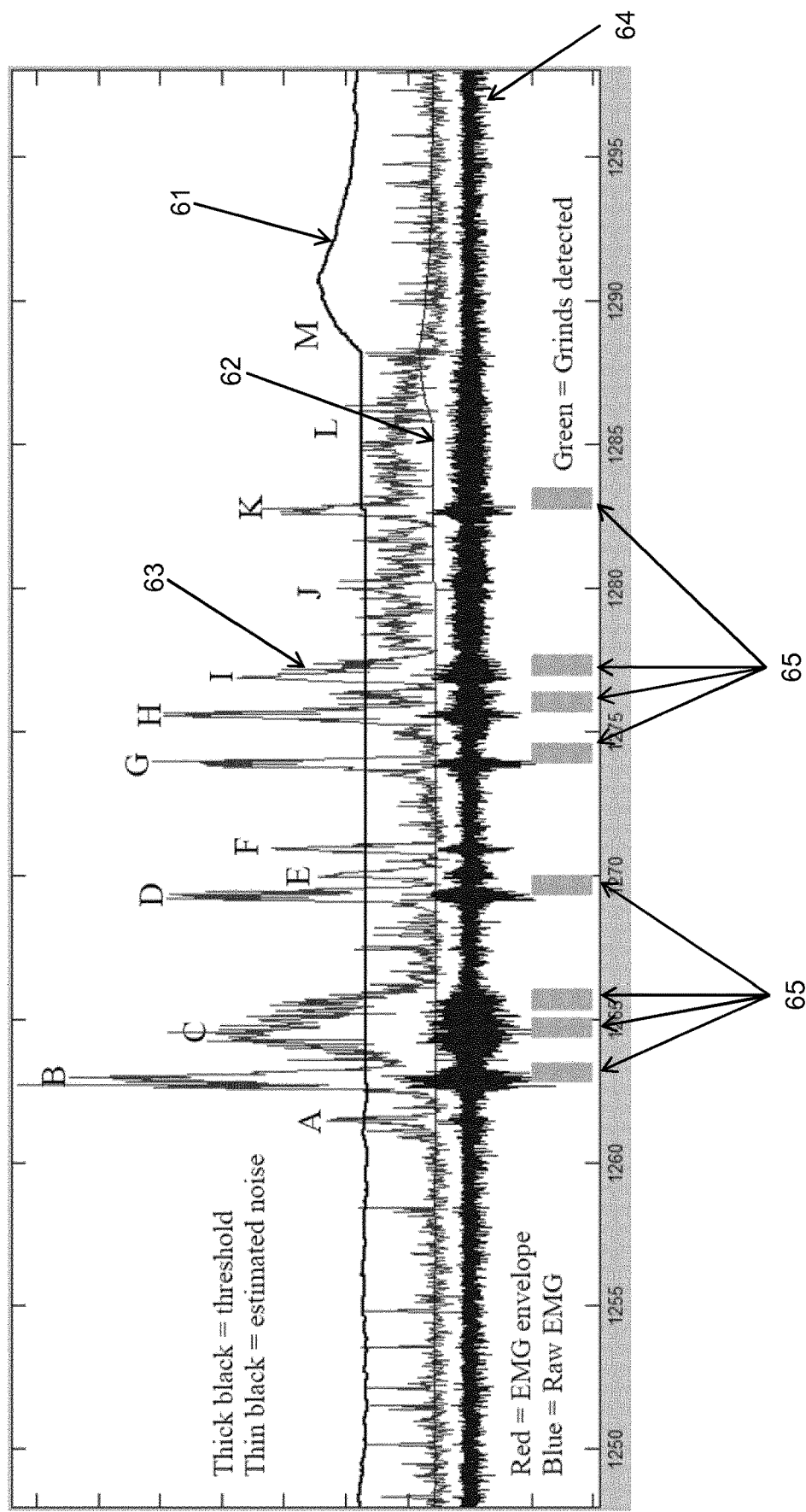
FIG. 6 shows another embodiment of the disclosed method.

An illustration of another embodiment of the method for automatic detection of teeth clenching is shown in FIG. 6. In FIG. 6, the data is EMG data obtained from EMG signals. As can be seen from FIG. 6, the estimated background level 62 is constantly changing with respect to time, except for these periods wherein the calculation is stopped, i.e. wherein the method is fixing the threshold level 61, and after which the calculations are restarted. It can be seen in FIG. 6 that eight events 65 related to grinding are detected in total. In this example, the raw signal 64 is sampled at 2000 Hz. The signal envelope 63 is calculated by a 64-point FFT and averaging pins 7-13, as this corresponds to an RMS value of frequencies between 218 and 406 Hz. The noise level 62 is calculated by low-pass filtering the envelope when no activity is detected for at least 5 seconds. Furthermore, the threshold 61 for an event detection of grinding and/clenching is 3 times higher and 2.5 seconds delayed compared to the noise level 62. An event detection of grinding and/clenching is assigned if the envelope 63 is above the threshold 61 for more than 0.25 seconds. Accordingly, the events noted as A, E and F are small bursts, and not related to events of grinding and/clenching because the durations are too short. The events noted as B, D, G, H, I and K are bursts that are related to events of grinding and/clenching because the durations are longer than 0.25 seconds. The event noted as C is long burst between 2-3 seconds, and accordingly detected as two bursts, since per definition a burst is defined as 1 second in duration. The events noted as J, L and M are changes in background level, and because the signal envelopes 63 are too low in amplitude, they are not assigned as events related to grinding and/clenching. In the time before the event A, only the noise level 62 is changing, and the threshold level 61 is therefore constantly adapting to it. When the background level 62 is elevated at the event L, the threshold level 61 at M is accordingly elevated.

EXAMPLE 7

Figure 7:
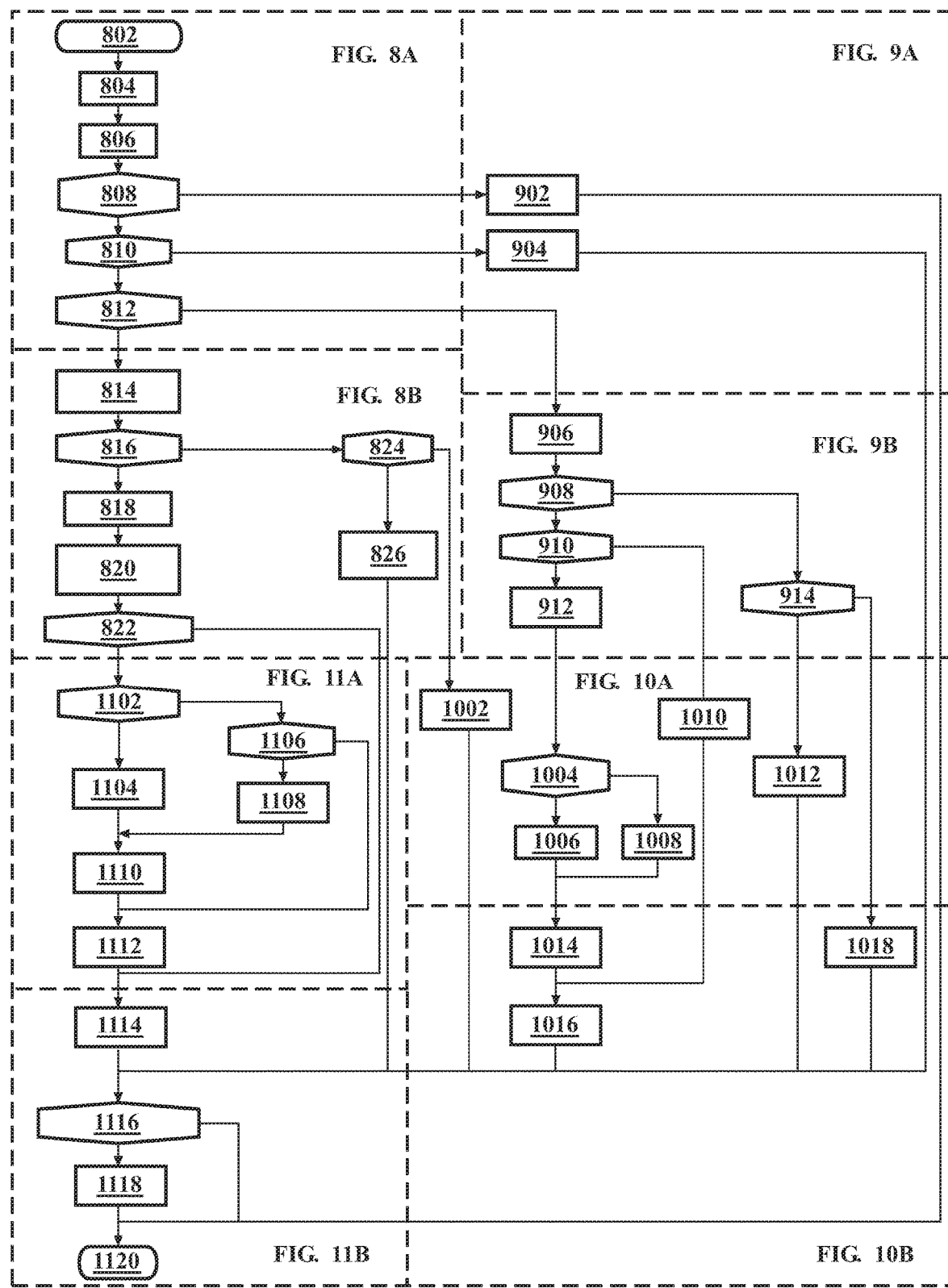
FIG. 7 shows an embodiment of the disclosed method illustrated as a flow chart, divided into eight blocks with the puncture lines, each block shown enlarged in FIGS. 8A, 8B, 9A, 9B, 10A, 10B, 11A, 11B respectively.
Figure 8A:
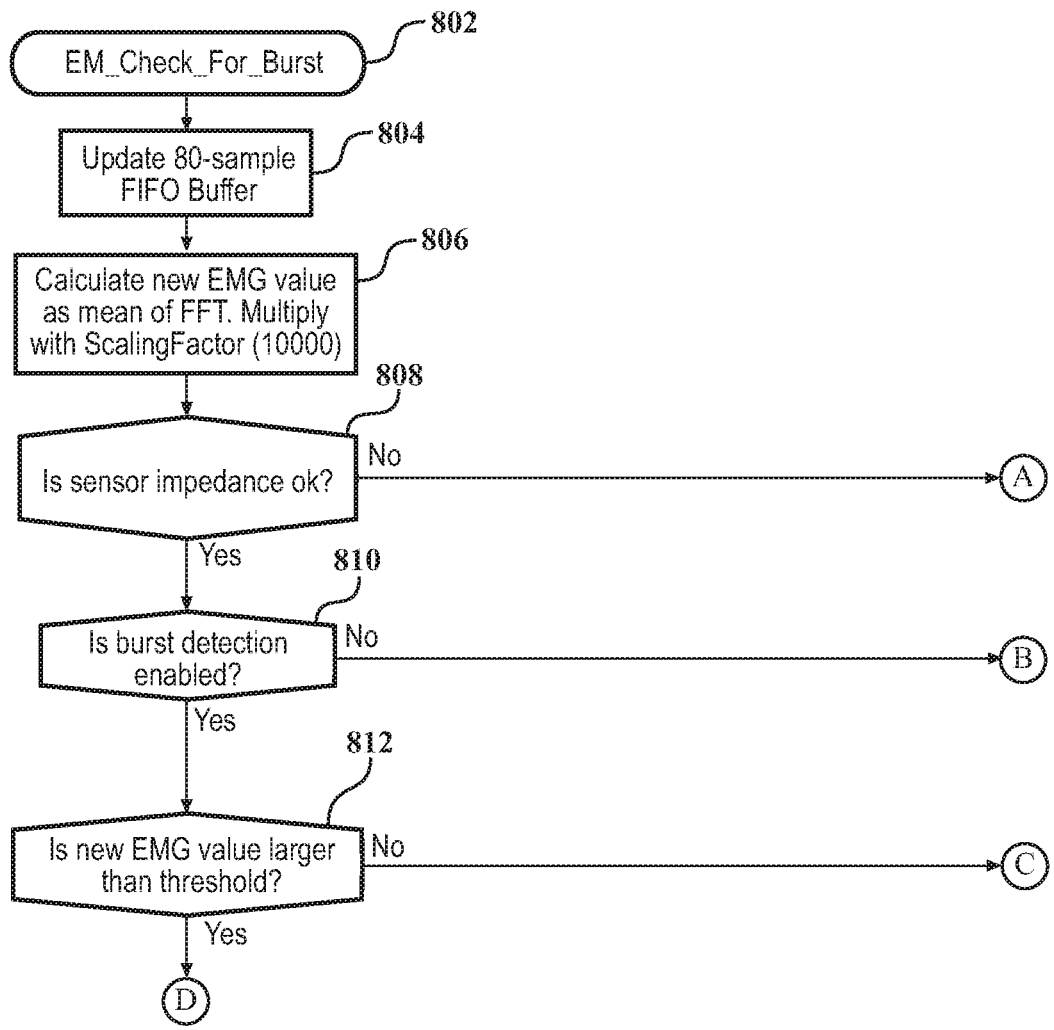
FIGS. 8A and 8B show embodiment of the disclosed method illustrate as a part of the flow chart from FIG. 7.
Figure 8B:
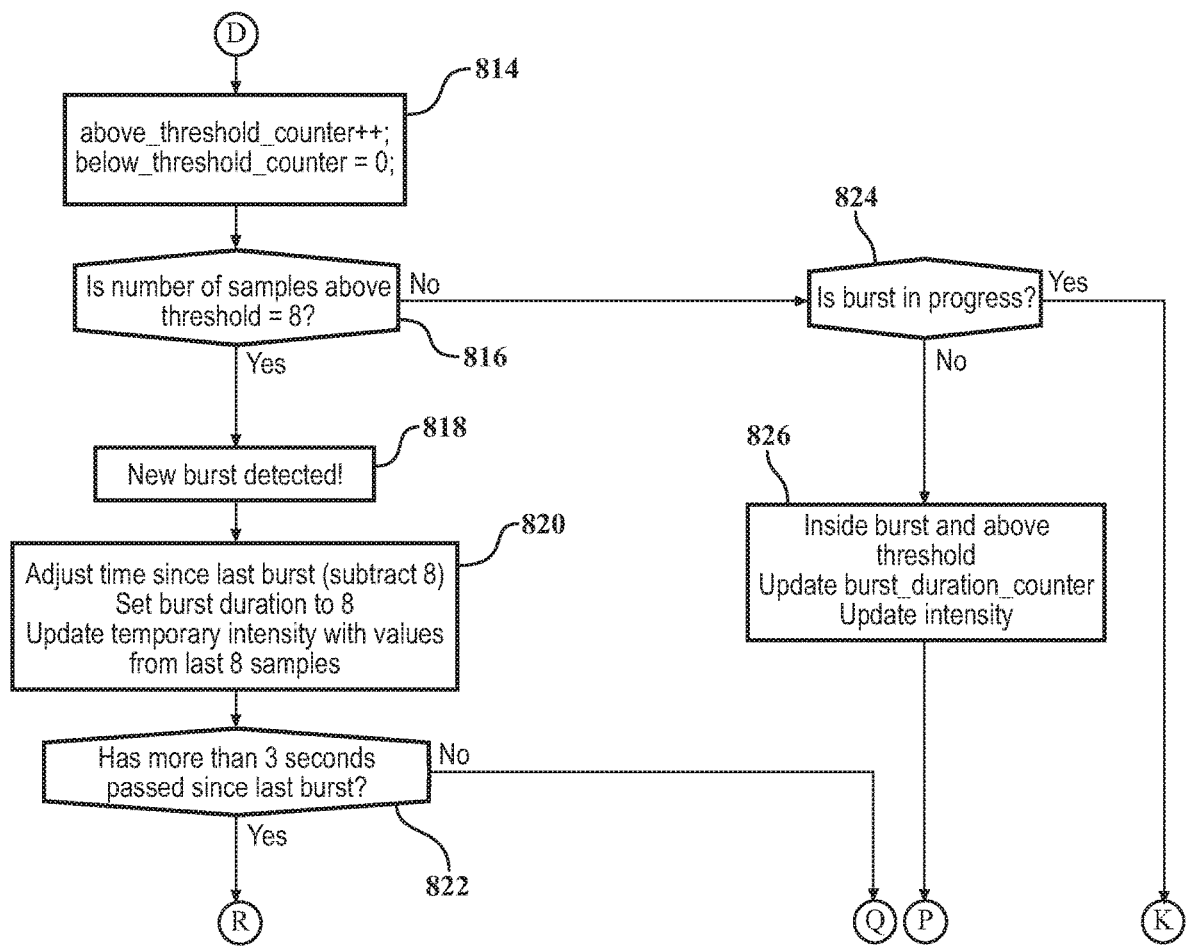
Figure 9B:
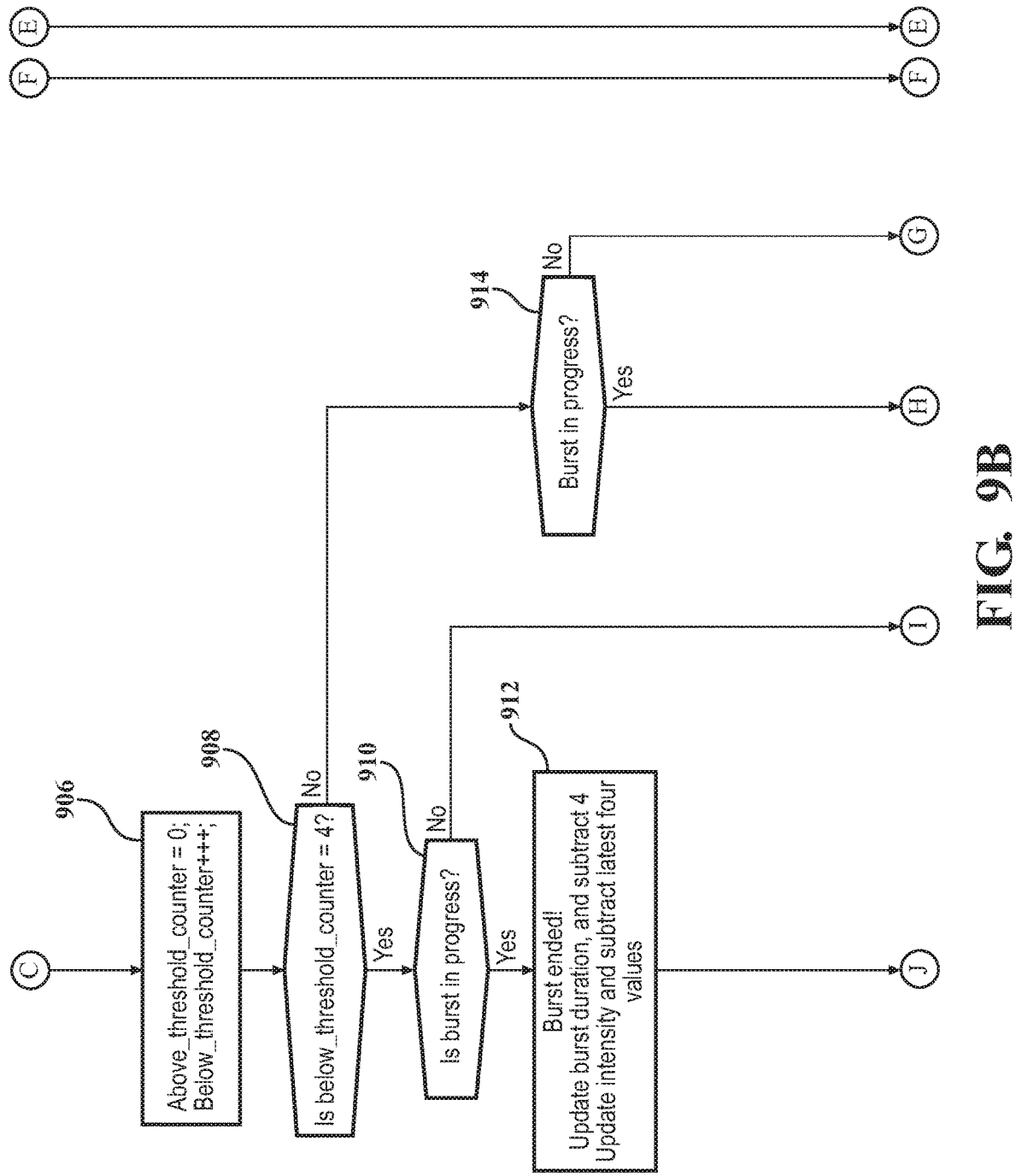
Figure 10A:
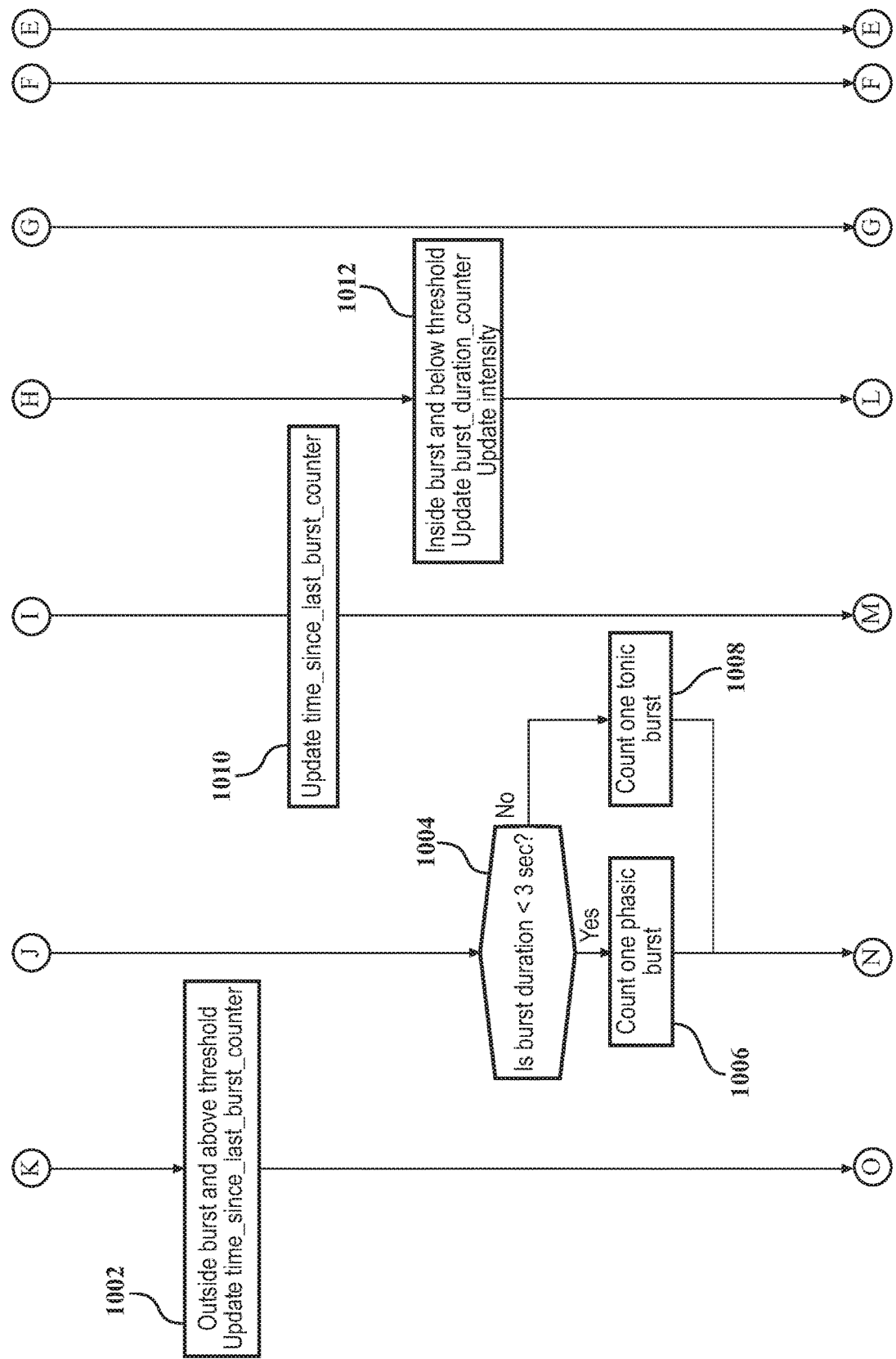
FIGS. 10A and 10B show an embodiment of the disclosed method illustrated as a part of the flow chart from FIG. 7.
Figure 10B:
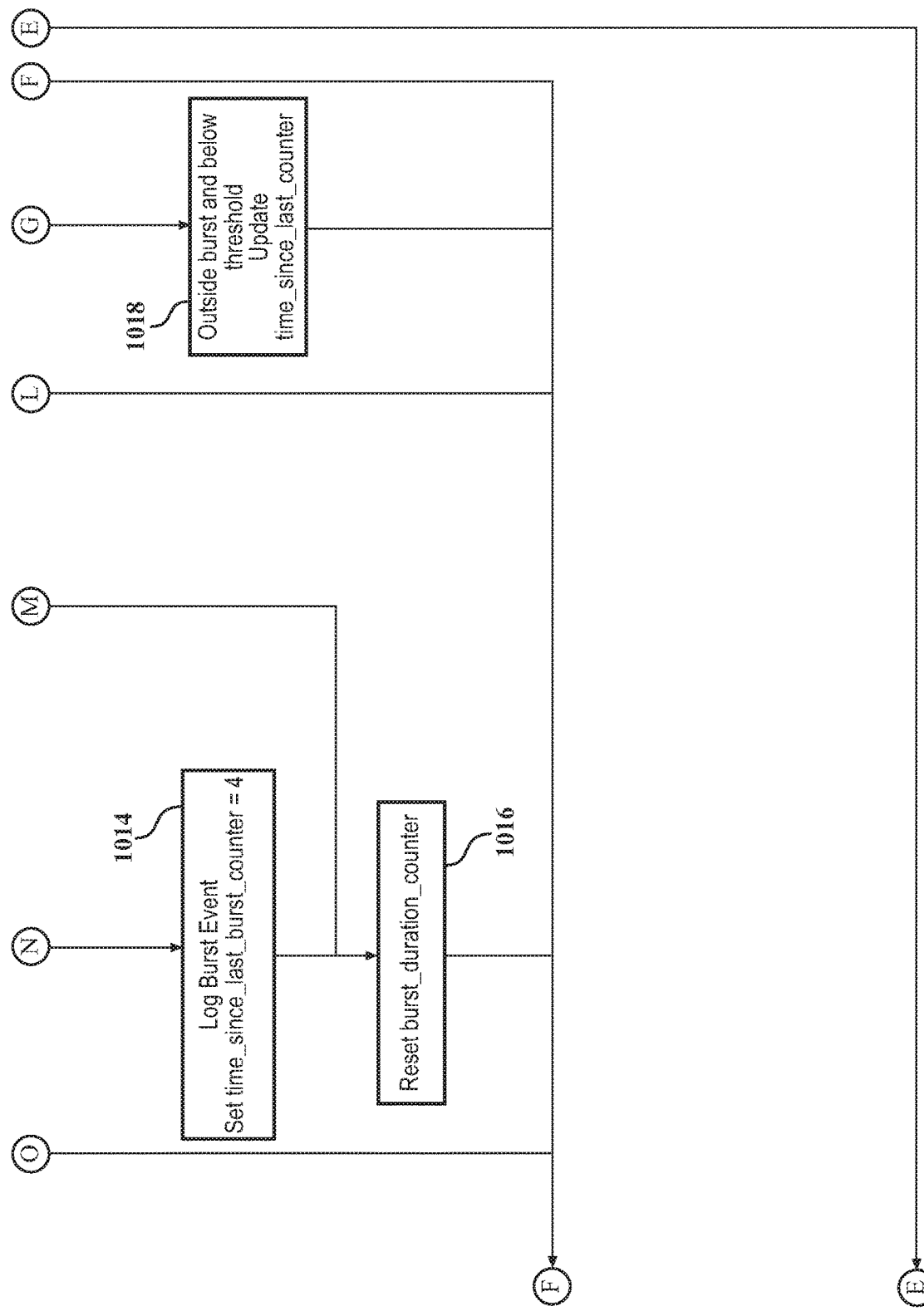
Figure 11A:
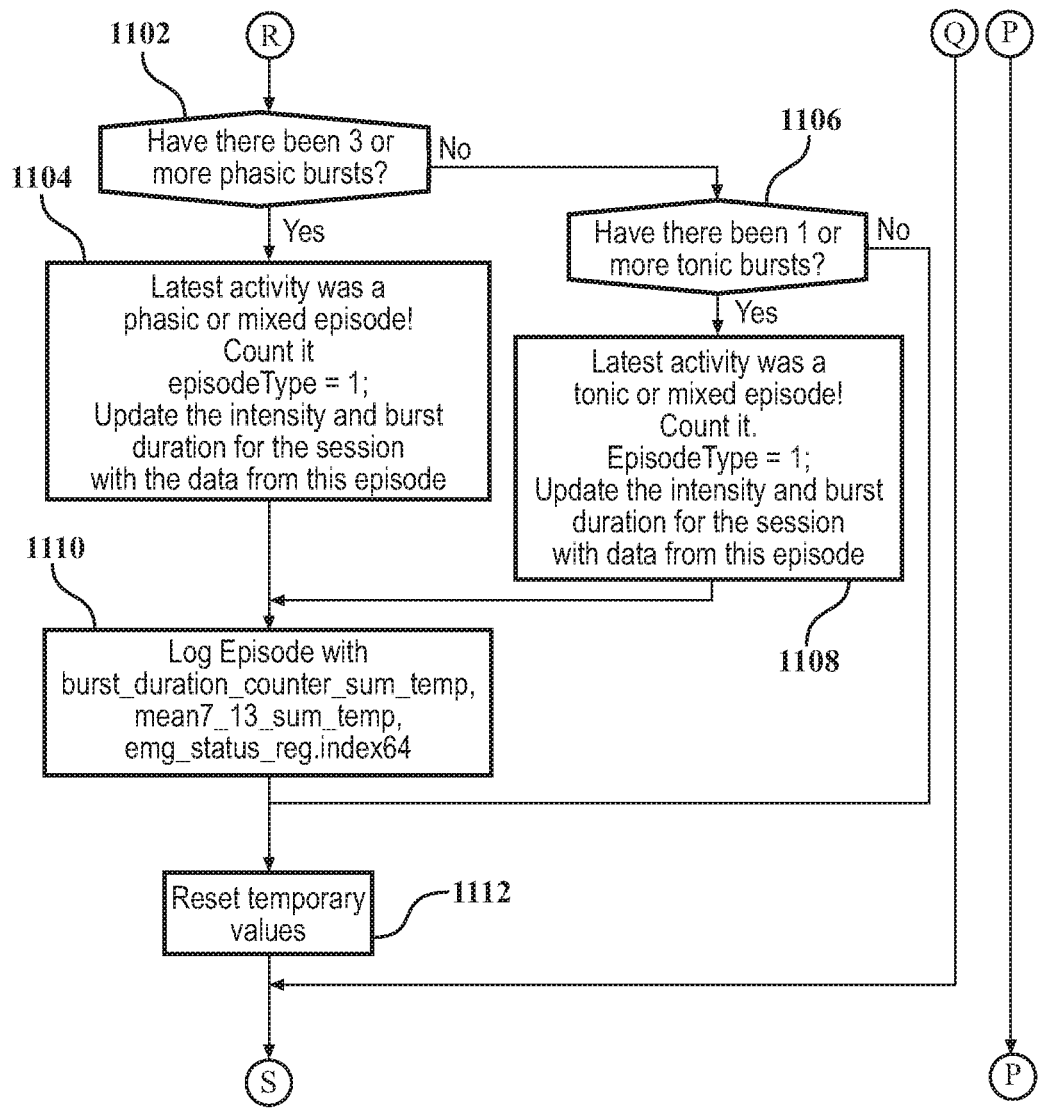
FIGS. 11A and 11B show an embodiment of the disclosed method illustrated as a part of the flow chart from FIG. 7.
Figure 11B:
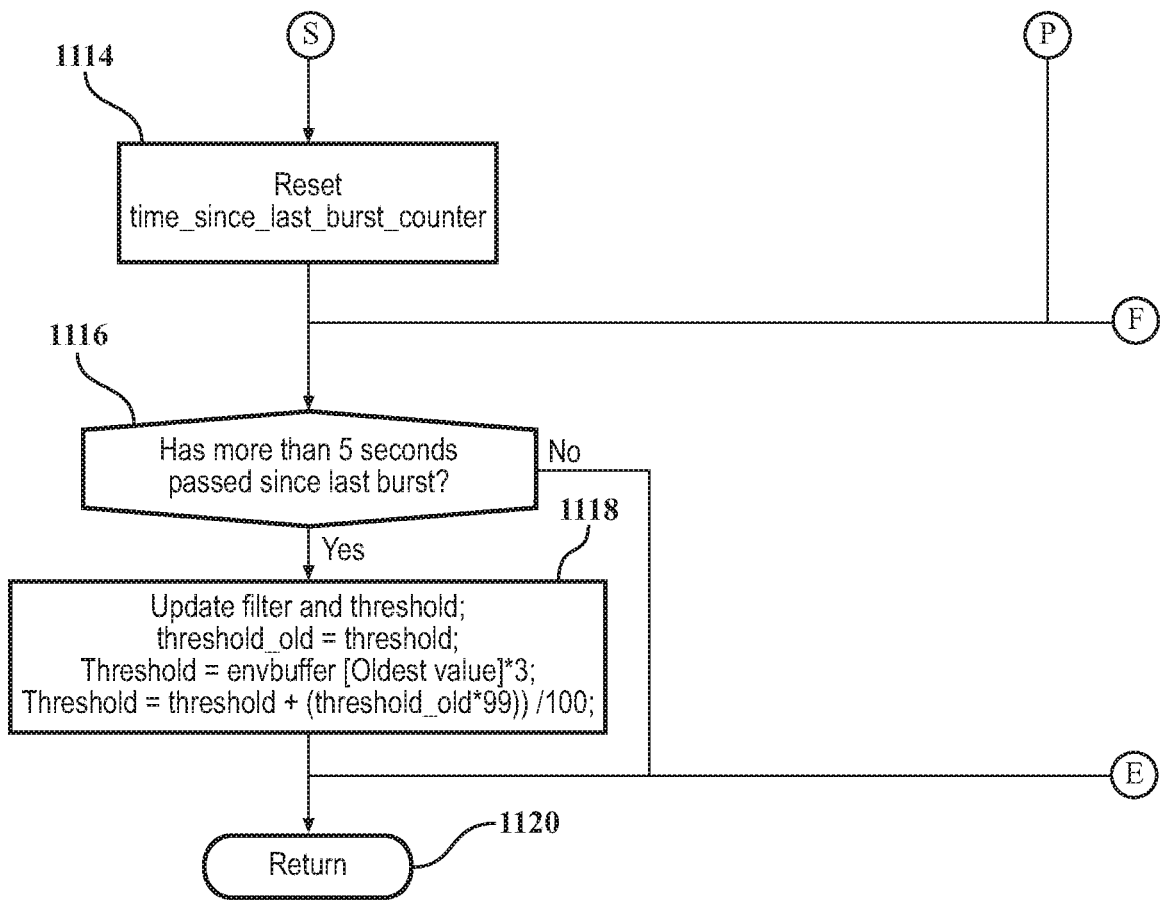

An embodiment of the method for automatic detection of teeth clenching, illustrated as a detailed flow chart, is shown in FIG. 7. The detailed flow chart is divided into eight blocks as shown with punctured lines, wherein the eight blocks are shown as enlarged in FIGS. 8A, 8B, 9A, 9B, 10A, 10B, 11A and 11B. The upper left blocks of FIG. 7 are shown enlarged in FIG. 8A and FIG. 8B, the upper right blocks of FIG. 7 are shown enlarged in FIG. 9A and FIG. 9B, the lower right blocks of FIG. 7 are shown enlarged in FIG. 10A and FIG. 10B, and the lower left blocks of FIG. 7 are shown enlarged in FIGS. 11A and 11B. The flow chart starts from the top, where a new signal envelope is calculated. This is an initial step to the disclosed method, which may be providing a frequency domain transform of the dataset, a frequency domain transform such as fast Fourier transform (FFT), discrete Fourier transform (DFT), discrete cosine transform (DCT) or discrete wavelet transform (DWT). The initial step as here illustrated may also comprise the step of averaging a predefined number of frequencies. The next step may be related to the measuring unit, since the measuring unit may comprise an electrode assembly configured to be attached to the skin of the subject and wherein the device may be configured to monitor the electrical connection between the electrode assembly and the skin, and wherein the processing unit may be configured to begin processing the signals when a connection between skin and electrode assembly has been detected. In case of poor electrical connection between the electrode assembly and the skin, the measuring unit restarts as shown in the flow chart. When beginning processing the signals, it may also check whether or not event detection is enabled as also shown in flow chart. In case of event detection being disabled, the time since last event is being updated as shown in the flow chart. From here, and in all circumstances, if no events of teeth clenching and/or teeth grinding has been assigned for a third predefined period of time $T_{silence}$, it may be possible to go back to start. In some cases, the step back to start may be followed with a calculation of a threshold level of biting force assigned to time $t=t_1$ based on a background level determined from the dataset at a prior time $t=t_1-T_{back}$, where $T_{back}$ is a first predefined period of time. From start, there may be a check of the level of biting, and if the level of biting force at time, t, exceeds the threshold level assigned to time $t_1$ for a second predefined period of time, $T_{clench/grind}$, then there may be assigned an event of teeth clenching to time t. If an event of teeth clenching has been assigned to time t, then there may be either a waiting of a predefined period of time $T_{wait}$, or a waiting until the level of biting is below the threshold for another predefined period of time $T_{end}$. If no events of teeth clenching and/or teeth grinding have been assigned for a third predefined period of time $T_{silence}$, the procedure repeats itself.

On the other hand, if events of teeth clenching and/or teeth grinding have been assigned for a third predefined period of time $T_{silence}$, then there may be a repeating of only some of the steps as shown in the flow chart.

Further Details of the Present Disclosure

The present disclosure may be described by the following items:

1. In a more general aspect the present disclosure relates to a computer implemented method for automatic detection of a predefined event in a dataset representing the level of muscular activity vs. time of a subject, the method comprising the steps of:
   a) calculating a threshold level of muscular activity assigned to time $t=t_1$ based on a background level determined from the dataset at a prior time $t=t_1-T_{back}$, where $T_{back}$ is a first predefined period of time,
   b) checking the level of muscular activity, and if the level of muscular activity at time, t, exceeds the threshold level assigned to time $t_1$ for a second predefined period of time, $T_{clench/grind}$, then assigning an event to time t,
   c) if an event has been assigned to time t, then either waiting a predefined period of time $T_{wait}$, or waiting until the level of muscular activity is below the threshold for another predefined period of time $T_{end}$,
   d) if no events have been assigned for a third predefined period of time $T_{silence}$, then repeating steps a)-c),
   e) if events have been assigned for a third predefined period of time $T_{silence}$, then repeating only steps b)-c).
2. A computer implemented method for automatic detection of teeth clenching and/or teeth grinding in a dataset representing the level of biting force vs. time of a subject, the method comprising the steps of
   a) calculating a threshold level of biting force assigned to time $t=t_1$ based on a background level determined from the dataset at a prior time $t=t_1-T_{back}$, where $T_{back}$ is a first predefined period of time,
   b) checking the level of biting, and if the level of biting force at time, t, exceeds the threshold level assigned to time t, for a second predefined period of time, $T_{clench/grind}$, then assigning an event of teeth clenching to time t,
   c) if an event of teeth clenching has been assigned to time t, then either waiting a predefined period of time $T_{wait}$, or waiting until the level of biting is below the threshold for another predefined period of time $T_{end}$,
   d) if no events of teeth clenching and/or teeth grinding have been assigned for a third predefined period of time $T_{silence}$, then repeating steps a)-c),
   e) if events of teeth clenching and/or teeth grinding have been assigned for a third predefined period of time $T_{silence}$, then repeating only steps b)-c).
3. The method according to any of the preceding items, wherein an event of teeth clenching and/or teeth grinding is characterized as one or more of the following: bruxism, daytime bruxism, nocturnal bruxism.
4. The method according to any of the preceding items, wherein the dataset represents muscular activity of the jaw vs. time of the subject.
5. The method according to any of the preceding items, wherein the dataset comprises electromyography (EMG) data.
6. The method according to any of the preceding items, wherein the dataset comprises one or more of the following: electromyography (EMG) data, electroencephalography (EEG) data, phonomyography (PMG) data, acceleration data, sound data and strain gauge data.
7. The method according to any of the preceding items, further comprising an initial step of providing a frequency domain transform of the dataset, a frequency domain transform such as fast Fourier transform (FFT), discrete Fourier transform (DFT), discrete cosine transform (DCT) or discrete wavelet transform (DWT).
8. The method according to item 7, wherein said initial step further comprising the step of averaging a predefined number of frequencies.
9. The method according to any of the preceding items, wherein the background level is determined by applying a low-pass filter to the dataset.
10. The method according to any of the preceding items, wherein $T_{end} \leq T_{clench/grind} < T_{wait} < T_{back} < T_{silence}$.
11. The method according to any of the preceding items, wherein $T_{end}$ is 0.125 s, or less than 0.25 s, or less than 0.5 s, or less than 0.4 s, or less than 0.35 s, or less than 0.3 s, or less than 0.25 s, or less than 0.2 s, or less than 0.15 s, or less than 0.1 s, or less than 0.05 s, or less than or less than 0.01 s.
12. The method according to any of the preceding items, wherein $T_{clench/grind}$ is 0.25 s, or less than 0.5 s, or less than 0.4 s, or less than 0.35 s, or less than 0.3 s, or less than 0.25 s, or less than 0.2 s, or less than 0.15 s, or less than 0.1 s, or less than 0.05 s.
13. The method according to any of the preceding items, wherein $T_{back}$ is 2.5 s, or less than 10 s, or less than 8 s, or less than 6 s, or less than 5 s, or less than 4 s, or less than 3 s, or less than 2 s, or less than 1 s.
14. The method according to any of the preceding items, wherein $T_{back}$ is at least 2.5 s, or at least 1 s, or at least 2 s, or at least 3 s, or at least 4 s, or at least 5 s, or at least 6 s, or at least 7 s, or at least 8 s, or at least 9 s, or at least 10 s.
15. The method according to any of the preceding items, wherein $T_{silence}$ is 5 s, or less than 10 s, or less than 8 s, or less than 6 s, or less than 5 s, or less than 4 s, or less than 3 s, or less than 2 s, or less than 1 s.
16. The method according to any of the preceding items, wherein $T_{silence}$ is at least 5 s, or at least 1 s, or at least 2 s, or at least 3 s, or at least 4 s, or at least 6 s, or at least 7 s, or at least 8 s, or at least 9 s, or at least 10 s.
17. The method according to any of the preceding items, wherein $T_{wait}$ is 1 s, or less than 10 s, or less than 8 s, or less than 6 s, or less than 5 s, or less than 4 s, or less than 3 s, or less than 2 s, or less than 1 s.
18. The method according to any of the preceding items, wherein $T_{wait}$ is at least 1 s, or at least 1 s, or at least 2 s, or at least 3 s, or at least 4 s, or at least 6 s, or at least 7 s, or at least 8 s, or at least 9 s, or at least 10 s.
19. The method according to any of the preceding items, wherein $T_{end}$ is between 0.4 and 0.6 times $T_{clench/grind}$ or wherein $T_{end}$ is between 0.3 and 0.7 times $T_{clench/grind}$ or wherein $T_{end}$ is between 0.45 and 0.55 times $T_{clench/grind}$ or wherein $T_{end}$ is 0.5 times $T_{clench/grind}$.
20. The method according to any of the preceding items, wherein $T_{back}$ is between 0.4 and 0.6 times $T_{silence}$ or between 0.3 and 0.7 times $T_{silence}$ or between 0.45 and 0.55 times $T_{silence}$ or wherein $T_{back}$ is 0.5 times $T_{silence}$.
21. The method according to any of the preceding items, wherein $T_{clench/grind}$ is between 0.05 and 0.15 times $T_{back}$ or between 0.02 and 0.25 times $T_{back}$ or between 0.08 and 0.12 times $T_{back}$ or wherein $T_{clench/grind}$ is 0.1 times $T_{back}$.
22. The method according to any of the preceding items, wherein $T_{wait}$ is less than $T_{back}$ and less than $T_{silence}$, such as between 0.15 and 0.25 times $T_{silence}$ or wherein $T_{wait}$ is 0.1 times $T_{silence}$.

23. The method according to any of the preceding items, wherein the threshold level is greater than and proportional to the background level.
24. The method according to any of the preceding items, wherein the threshold value is defined to be at least 1.5, 2, 3, 4 or at least 5 times the background level.
25. The method according to any of the preceding items, wherein the automatic detection of teeth clenching and/or teeth grinding is a real-time process carried out on a stream of data continuously received.
26. The method according to any of the preceding items, wherein the dataset is a stream of data continuously received from a measuring unit.
27. A data-processing system comprising a processor and a memory and being configured to perform the method according to any of preceding items.
28. A device for monitoring facial activity related to teeth clenching and/or teeth grinding of a subject comprising:
    a measuring unit for providing signals indicative of said facial activity, and
    a processing unit for processing said signals in order to detect said teeth clenching and/or teeth grinding.
29. The device according item 28, wherein the processing unit is configured to automatically determine a threshold level according to any of preceding items 1 to 26.
30. The device according to items 28-29, wherein the processing unit is configured to perform the method of any of preceding items 1 to 26.
31. The device according to items 28-30, wherein the frequency domain transform according to item 7 is hardware implemented in the processing unit.
32. The device according to items 28-31, wherein the signals indicative of said facial activity represents the level of biting force vs. time of the subject and wherein the processing unit is configured to perform the method of any of the preceding items 1 to 26 and wherein an event of teeth clenching and/or teeth grinding is an event of bruxism.
33. The device according to items 28-32, wherein the measuring unit comprises at least one electrode assembly for providing said signals.
34. The device according to items 28-33, wherein the facial activity is muscle activity, teeth grinding, and/or teeth clenching.
35. The device according to items 28-34, further comprising a feedback unit for providing a feedback signal in response to detecting said bruxism.
36. The device according to items 28-35, wherein the measuring unit is configured to provide a feedback signal in response to detecting said bruxism.
37. The device according to items 28-36, wherein the feedback signal is a visual, tactile, acoustic, and/or medical, such as a relaxing agent, feedback delivered to the subject.
38. The device according to items 28-37, wherein the processing unit is integrated/incorporated in the measuring unit.
39. The device according to items 28-38, wherein the measuring unit comprises an electrode assembly configured to be attached to the skin of the subject and wherein the device is configured to monitor the electrical connection between the electrode assembly and the skin, and wherein the processing unit is configured to begin processing the signals when a connection between skin and electrode assembly has been detected.
40. The device according items 28-39, further comprising an internal chargeable electrical power source, such as a battery, for powering the device.
41. A bruxism system comprising the device according to item 40 and a storage case for housing and charging the device, wherein the device is configured to be automatically switched on when removed from the storage case.
42. The bruxism system according to item 41, wherein the device and the storage case are configured such that the device is automatically switched off when installed in the storage case if the storage case is not connected to an external electrical power source.
43. The bruxism system according to any of items 41 to 42, wherein the storage case comprises an electrical circuit configured to detect an electrical connection between the storage case and the device.
44. The bruxism system according to any of items 41 to 43, wherein the device comprises at least one magnet and the storage case comprises a sensor unit for sensing the presence of a magnetic field, such as a hall-effect switch, and wherein the storage case sensor is configured to detect the presence of the device in the storage case.
45. The bruxism system according to any of items 41 to 44, wherein the device comprises a mechanical switch that is configured to be engaged by the device when the device is installed in the storage case.
46. The bruxism system according to any of items 41 to 45, wherein the storage case and the device is configured such that the internal chargeable electrical power source in the device is charged by electrical power transmitted wirelessly from the storage case to the device.

The invention claimed is:
1. A computer implemented method adapted for an individual for automatic detection of a predefined event associated with a level of muscular activity of the individual, the method comprising the steps of:
   a) continuously monitoring, by a measuring unit, the level of muscular activity of a subject over a monitoring period of time;
   b) automatically and continuously, by a processing unit, calculating a background level of the monitored muscular activity;
   c) automatically and continuously, by the processing unit, calculating a threshold level of muscular activity assigned to time $t_1$ based on the background level determined at a prior time $t_1-T_{back}$, where $T_{back}$ is a first predefined period of time;
   d) repeating b) and c) to continuously update the threshold level until the level of muscular activity at time t exceeds the threshold level assigned to time $t_1$ for a second predefined period of time, $T_{clench/grind}$, then, by the processing unit:
      (1) setting the threshold level assigned to time $t_1$ as a fixed level,
      (2) then assigning a clench/grind event to time t,
      (3) then either waiting a predefined period of time, $T_{wait}$, or waiting until the level of muscular activity is below the fixed level for another predefined period of time, $T_{end}$,
      (4) then resetting an event duration counter;
   e) continuously, by the measuring unit, monitoring the muscular activity and comparing the activity level with the fixed level,

(1) when the level of muscular activity exceeds the fixed level before an end of a third period of time, $T_{silence}$, repeating from step d) (2), (2) when the level of muscular activity remains below the fixed level for the third predefined period of time, $T_{silence}$, then continuously, by the processing unit, updating the background level of the monitored muscular activity and updating the threshold level of muscular activity assigned to time $t_1$ based on the background level determined at a prior time $t_1 - T_{back}$, then continuing from step b);

such that the threshold level of muscular activity is adapted to the background level of muscular activity thereby providing automatic detection of clench/grind events associated with the level of muscular activity of the individual.

2. The method according to claim 1, wherein the level of muscular activity is a level of biting force.

3. The method according to claim 1, wherein the clench/grind event is characterized as one or more of the following: bruxism, daytime bruxism, nocturnal bruxism.

4. The method according to claim 1, wherein $T_{end} \leq T_{clench/grind} < T_{wait} < T_{back} < T_{silence}$.

5. The method according to claim 1, wherein $T_{end}$=0.125 s, $T_{clench/grind}$=0.25 s, $T_{back}$=2.5 s, $T_{silence}$=5 s and $T_{wait}$=1 s.

6. The method according to claim 1, wherein $T_{end}$ is between 0.4 and 0.6 times $T_{clench/grind}$.

7. The method according to claim 1, wherein $T_{back}$ is between 0.4 and 0.6 times $T_{silence}$.

8. The method according to claim 1, wherein $T_{clench/grind}$ is between 0.05 and 0.15 times $T_{back}$.

9. The method according to claim 1, wherein $T_{wait}$ is less than $T_{back}$ and less than $T_{silence}$.

10. The method according to claim 1, wherein the threshold level is greater than and proportional to the background level.

11. The method according to claim 1, wherein the automatic detection is a real-time process carried out on a stream of data continuously received by the processing unit.

12. The method according to claim 1, wherein the predefined event is in a dataset representing muscular activity of a jaw vs. time of the subject.

13. The method according to claim 12, wherein the dataset comprises one or more of the following: electromyography (EMG) data, electroencephalography (EEG) data, phonomyography (PMG) data, acceleration data, sound data and strain gauge data.

14. The method according to claim 12, further comprising initial step of providing a frequency domain transform of the dataset, the frequency domain transform selected from a fast Fourier transform (FFT), a discrete Fourier transform (DFT), a discrete cosine transform (DCT), and a discrete wavelet transform (DWT).

15. The method according to claim 1, wherein $T_{wait}$ is between 0.15 and 0.25 times $T_{silence}$.

16. The method according to claim 1, wherein the background level is a smoothed signal calculated using a low-pass filter.

17. A device for monitoring facial activity related to a clench/grind event of a subject comprising:
a measuring unit for providing signals indicative of said facial activity, and
a processing unit for processing said signals in order to detect said clench/grind event, wherein the processing unit is configured to automatically determine a threshold level according to claim 1.

18. The device according to any claim 17, wherein the signals indicative of said facial activity represents a level of biting force vs. time of the subject and wherein the processing unit is configured to perform the method of claim 1, and wherein a clench/grind event is an event of bruxism.

19. The device according to claim 18, wherein the measuring unit comprises an electrode assembly configured to be attached to a skin surface of the subject and wherein the device is configured to monitor an electrical connection between the electrode assembly and the skin, and wherein the processing unit is configured to begin processing the signals when the electrical connection between skin and electrode assembly has been detected.

20. The device according to claim 17, wherein the measuring unit is configured to provide a feedback signal in response to detecting said clench/grind event, the feedback signal being a visual, tactile, acoustic, and/or medical feedback delivered to the subject.

21. The device according to claim 17, wherein the processing unit is integrated in the measuring unit.

* * * * *